United States Patent
Miyazaki et al.

(10) Patent No.: US 11,617,613 B2
(45) Date of Patent: Apr. 4, 2023

(54) MEDICAL INSTRUMENT AND A TREATMENT INSTRUMENT, INCLUDING A BENDABLE END EFFECTOR

(71) Applicant: Olympus Corporation, Hachioji (JP)

(72) Inventors: Akira Miyazaki, Yokohama (JP); Yuki Kawaguchi, Koshu (JP); Kazuhiro Tanaka, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 718 days.

(21) Appl. No.: 16/685,324

(22) Filed: Nov. 15, 2019

(65) Prior Publication Data

US 2020/0078087 A1 Mar. 12, 2020

Related U.S. Application Data

(63) Continuation of application No. PCT/JP2017/021512, filed on Jun. 9, 2017.

(51) Int. Cl.
*A61B 17/29* (2006.01)
*A61B 18/14* (2006.01)
(Continued)

(52) U.S. Cl.
CPC ............. *A61B 18/1447* (2013.01); *A61B 2017/00973* (2013.01); *A61B 2017/2908* (2013.01);
(Continued)

(58) Field of Classification Search
CPC ........ A61B 18/1447; A61B 2017/2908; A61B 2017/2925; A61B 2017/2938;
(Continued)

(56) References Cited

U.S. PATENT DOCUMENTS 5,499,998 A * 3/1996 Meade ............... A61B 17/29
606/208
5,735,849 A * 4/1998 Baden ............... A61B 18/1442
606/205

(Continued)

FOREIGN PATENT DOCUMENTS

JP 2007-203053 A 8/2007
JP 2013-220107 A 10/2013
(Continued)

OTHER PUBLICATIONS

Aug. 1, 2017 International Search Report issued in International Patent Application No. PCT/JP2017/021512.
(Continued)

*Primary Examiner* — Timothy J Neal
*Assistant Examiner* — Mitchell Brian Hoag
(74) *Attorney, Agent, or Firm* — Oliff PLC

(57) ABSTRACT

A medical instrument comprises a housing and an elongated sheath configured to be attached to the housing. The elongated sheath includes opposed distal end and proximal end along a longitudinal axis. An end effector is configured to be attached to the distal end of the elongated sheath. The end effector includes a pair of grasps. A direction changer is used to change a direction of the end effector with respect to the distal end of the elongated sheath. A first drive shaft movable in the elongated sheath in ganged relation for opening and closing movement of the pair of grasps. A second drive shaft movable in the elongated sheath in ganged relation for angular movement of the end effector by the direction changer with respect to the elongated sheath. An operating member is configured to actuate the second drive shaft between a bent positions and a neutral position.

20 Claims, 27 Drawing Sheets

(51) Int. Cl.
    *A61B 90/00*    (2016.01)
    *A61B 17/00*    (2006.01)
    *A61B 18/12*    (2006.01)

(52) U.S. Cl.
    CPC ................ *A61B 2017/2925* (2013.01); *A61B 2017/2938* (2013.01); *A61B 2018/1226* (2013.01); *A61B 2090/035* (2016.02)

(58) Field of Classification Search
    CPC .. A61B 2017/00314; A61B 2017/2902; A61B 2017/2912; A61B 2017/2913; A61B 2017/292; A61B 2017/2927; A61B 2017/2932; A61B 17/29; A61B 2017/00973; A61B 2018/1226
    See application file for complete search history.

(56) References Cited

U.S. PATENT DOCUMENTS

| | | | |
|---|---|---|---|
| 2011/0290857 A1 | 12/2011 | Shelton, IV et al. | |
| 2013/0304105 A1* | 11/2013 | Onuma | A61B 18/1445 606/169 |
| 2015/0066022 A1 | 3/2015 | Shelton, IV et al. | |
| 2016/0074653 A1* | 3/2016 | Anglese | A61B 18/1206 606/51 |
| 2016/0375273 A1* | 12/2016 | Hirai | A61N 7/02 606/29 |
| 2017/0071617 A1* | 3/2017 | Kawaguchi | A61B 18/085 |
| 2018/0074543 A1* | 3/2018 | Lamser | A61B 18/1445 |
| 2019/0159822 A1* | 5/2019 | Honda | A61B 18/085 |
| 2019/0261981 A1* | 8/2019 | Chen | A61B 17/07207 |
| 2019/0307475 A1* | 10/2019 | Kitamura | A61B 17/29 |
| 2020/0113622 A1* | 4/2020 | Honegger | A61B 18/1442 |

FOREIGN PATENT DOCUMENTS

| | | |
|---|---|---|
| JP | 2013-220108 A | 10/2013 |
| WO | 03/026519 A1 | 4/2003 |

OTHER PUBLICATIONS

Dec. 10, 2019 International Preliminary Report on Patentability issued in International Patent Application No. PCT/JP2017/021512.

* cited by examiner

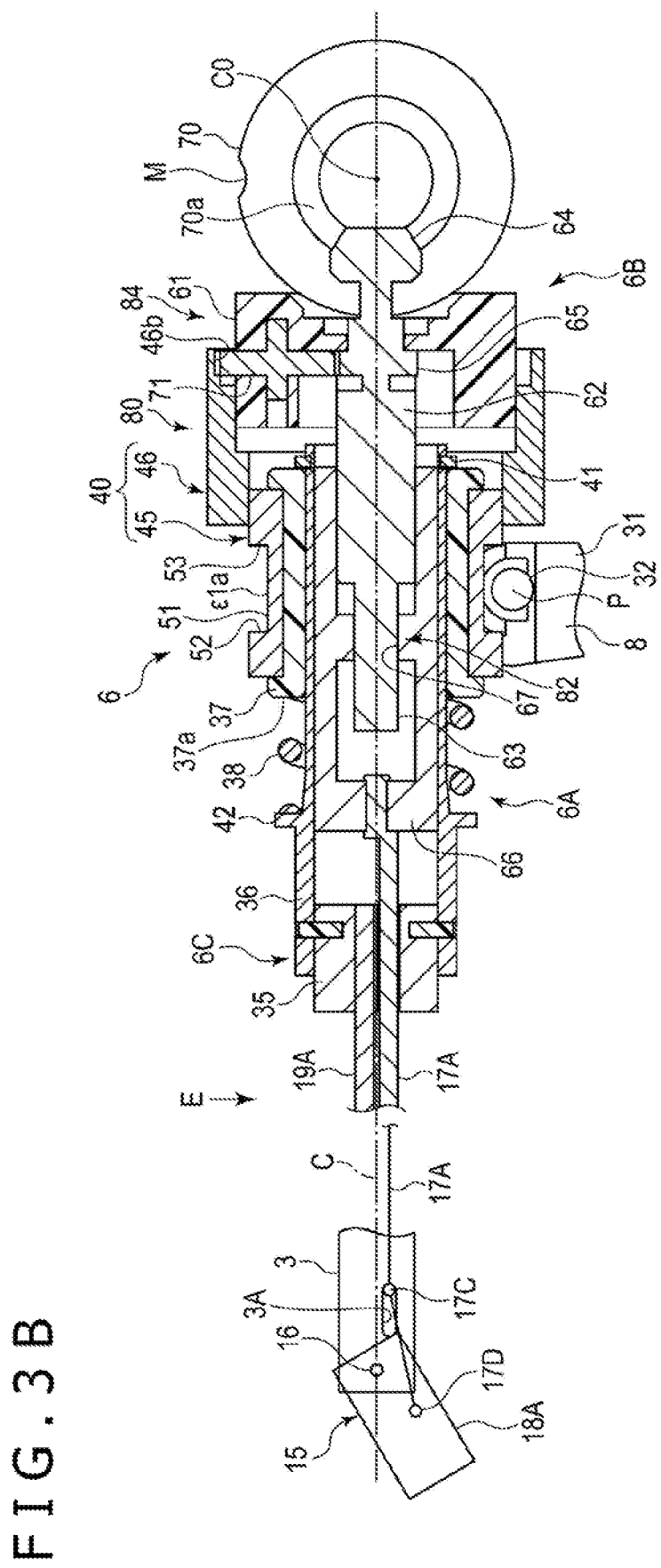

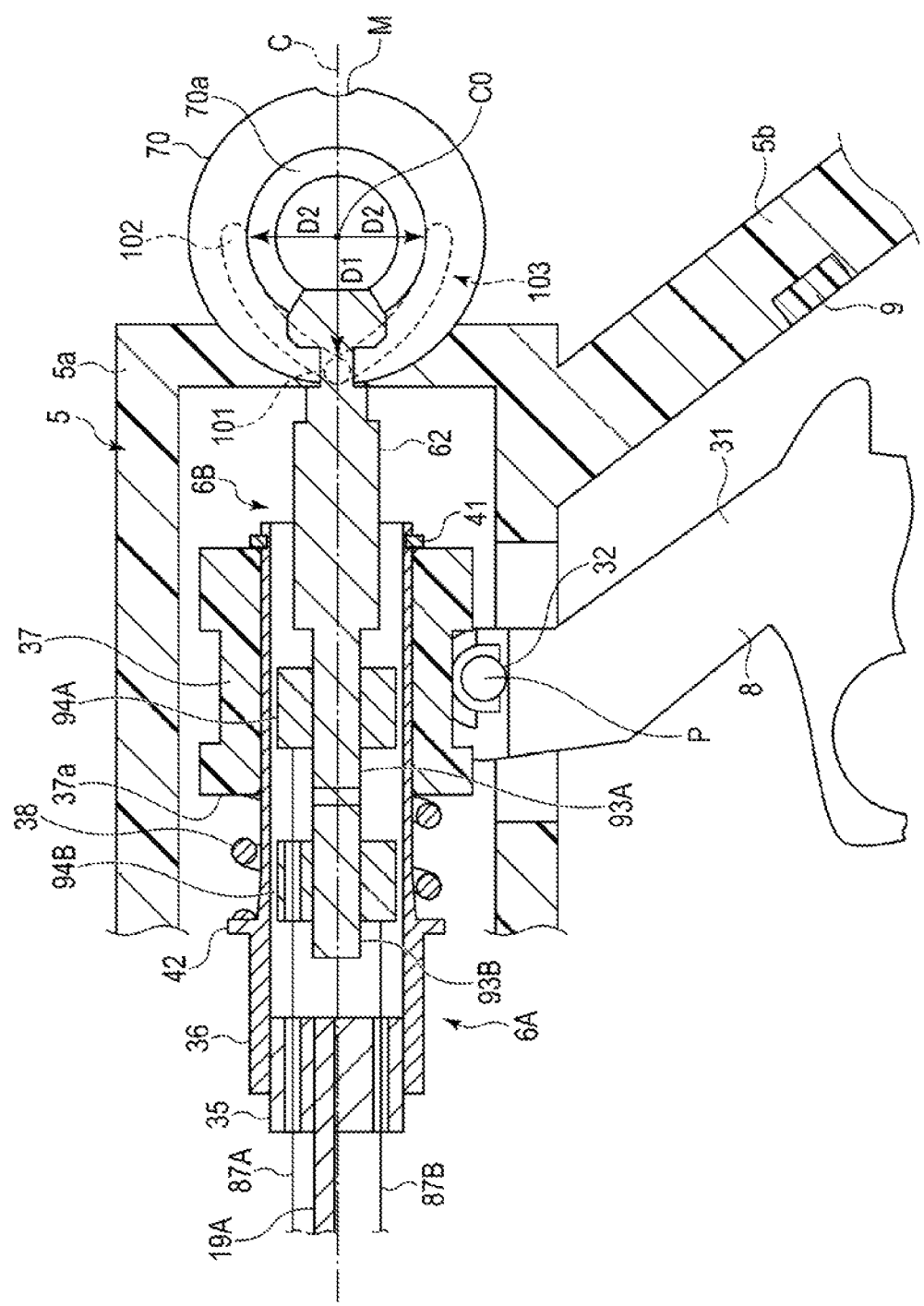

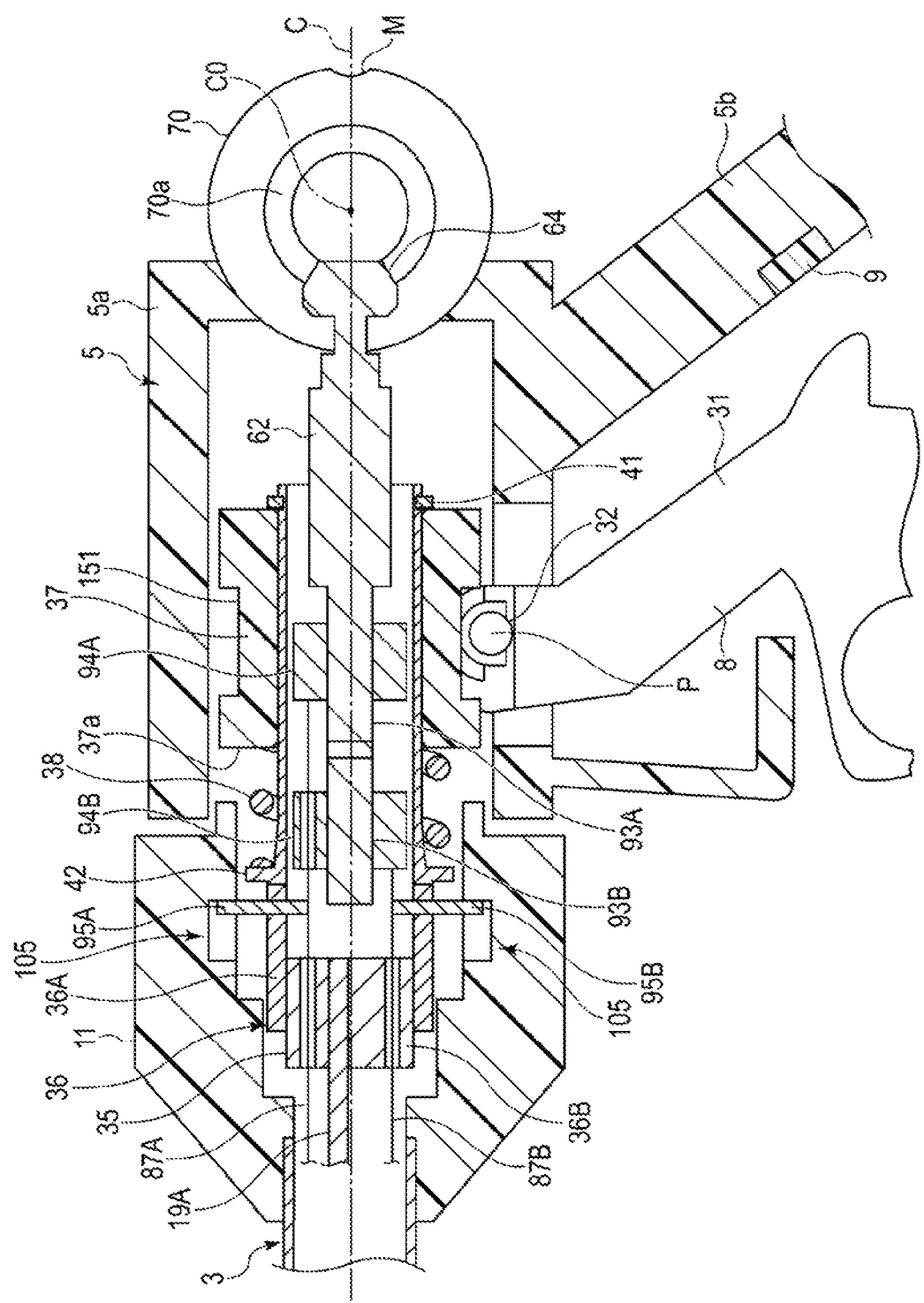

MEDICAL INSTRUMENT AND A TREATMENT INSTRUMENT, INCLUDING A BENDABLE END EFFECTOR

CROSS-REFERENCE TO RELATED APPLICATION

This application is a continuation application of PCT Application No. PCT/JP2017/021512 filed on Jun. 9, 2017, which is hereby incorporated by reference in its entirety.

TECHNICAL FIELD

The disclosed technology relates to a medical instrument including an end effector that can be bent with respect to a sheath.

DESCRIPTION OF THE RELATED ART

For example, US Patent Application 2015/0066022 A1 discloses a medical instrument having an end effector that includes a pair of grasps on a distal-end side of a sheath, for gripping an object such as a biological tissue, also known as, biotissue. A gripping force is transmitted to act between the pair of grasps by an axial force of a drive shaft based on a gripping operation of a movable handle. The medical instrument also includes an operating member on a proximal-end side that is operated to bend the end effector including the pair of grasps at a distal end of the sheath. Therefore, the end effector is movable at the distal end of the sheath between a neutral position in which the end effector extends straight along a longitudinal axis of the sheath and a bent position in which the end effector is bent off the longitudinal axis of the sheath.

The axial force of the drive shaft that affects the gripping force between the pair of grasps tends to be lower when the end effector is in the bent position than when the end effector is in the neutral position. Therefore, in a case where an object such as a biotissue is gripped between the pair of grasps, the axial force of the drive shaft, i.e., the gripping force between the pair of grasps, should desirably be adjusted appropriately, e.g., to a constant value, between the neutral position and the bent position.

Accordingly, there is a need for a medical instrument capable of appropriately adjusting an axial force transmitted to a drive shaft while a pair of grasps holding a treatment target therebetween and when an end effector is either in a neutral or a bent position.

BRIEF SUMMARY OF EMBODIMENTS

One aspect of the disclosed technology is directed to a medical instrument comprises a housing and an elongated sheath configured to be attached to the housing. The elongated sheath includes opposed distal end and proximal end along a longitudinal axis. An end effector is configured to be attached to the distal end of the elongated sheath. The end effector includes a pair of grasps. A direction changer used to change a direction of the end effector with respect to the distal end of the elongated sheath. A first drive shaft movable in the elongated sheath in ganged relation for opening and closing movement of the pair of grasps. A second drive shaft movable in the elongated sheath in ganged relation for angular movement of the end effector by the direction changer with respect to the elongated sheath. An operating member is configured to actuate the second drive shaft between bent positions to which the end effector is angularly moved and a neutral position to which the end effector extends along the longitudinal axis with respect to the sheath. A slider is movable with respect to the first drive shaft. An adjusting mechanism adjusts a movable range of the slider with respect to the first drive shaft depending on an operated state of the operating member.

Another aspect of the disclosed technology is directed to a medical instrument comprises a housing having a grip integrally attached thereto. A movable handle is attached to the housing and is angularly movable with respect to the housing. An elongated sheath having respective distal and proximal ends along a longitudinal axis. The elongated sheath is attached to the housing via the proximal end. An end effector is configured to be attached to the distal end of the elongated sheath. The end effector includes a pair of grasps. A direction changer changes a direction of the end effector with respect to the distal end of the elongated sheath. A first drive shaft is movable in the elongated sheath in ganged relation for opening and closing movement of the pair of grasps. A second drive shaft is movable in the elongated sheath in ganged relation for angular movement of the end effector by the direction changer with respect to the elongated sheath. An operating member is configured to actuate the second drive shaft between bent positions to which the end effector is angularly moved and a neutral position in which the end effector extends along the longitudinal axis with respect to the sheath. A slider being movable with respect to the first drive shaft. An adjusting mechanism adjusts a movable range of the slider with respect to the first drive shaft depending on an operated state of the operating member. The medical instrument further comprises a power supply device being attached to the housing via a cable. The medical instrument further includes an operating device such as a foot switch configured to be attached to the power supply device.

A further aspect of the disclosed technology is directed to a treatment tool comprises a medical instrument. The medical instrument includes a power supply device and a housing is attached to the power supply device. The housing having a grip integrally attached thereto. A movable handle is attached to the housing and is angularly movable with respect to the housing. An elongated sheath having respective distal and proximal ends along a longitudinal axis. The elongated sheath is attached to the housing via the proximal end. An end effector is configured to be attached to the distal end of the elongated sheath. The end effector includes a pair of grasps. A direction changer changes a direction of the end effector with respect to the distal end of the elongated sheath. A first drive shaft being movable in the elongated sheath in ganged relation for opening and closing movement of the pair of grasps. A second drive shaft being movable in the elongated sheath in ganged relation for angular movement of the end effector by the direction changer with respect to the elongated sheath. An operating member is configured to actuate the second drive shaft between bent positions to which the end effector is angularly moved and a neutral position in which the end effector extends along the longitudinal axis with respect to the sheath. A slider being movable with respect to the first drive shaft and an adjusting mechanism adjusts a movable range of the slider with respect to the first drive shaft depending on an operated state of the operating member.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

FIG. 3B is a schematic view illustrating the cross section of the actuating mechanism disposed in the housing of the treatment tool of the treatment system according to the first embodiment and also illustrating a state, or a first bent position, of the end effector with respect to the actuating mechanism, as viewed from a direction of an arrow E in an area illustrated in cross section.

FIG. 13A is a schematic view illustrating a cross section of an actuating mechanism disposed in a housing in a case where an end effector of a treatment tool of a treatment system according to a second embodiment is in a neutral position.

FIG. 16A is a schematic view illustrating a cross section of an actuating mechanism disposed in a housing in a case where an end effector of a treatment tool of a treatment system according to a third modification of the second embodiment is in a neutral position.

DETAILED DESCRIPTION OF THE EMBODIMENTS

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

It is an object of the disclosed technology to provide a medical instrument that is capable of adjusting an axial force transmitted to a drive shaft opening and closing a pair of grasps relatively to each other, in a case where an end effector is in a neutral position and in a case where the end effector is in a bent position.

First Embodiment

A first embodiment of the disclosed technology will be described below with reference to FIGS. 1 through 5B.

Figure 1:
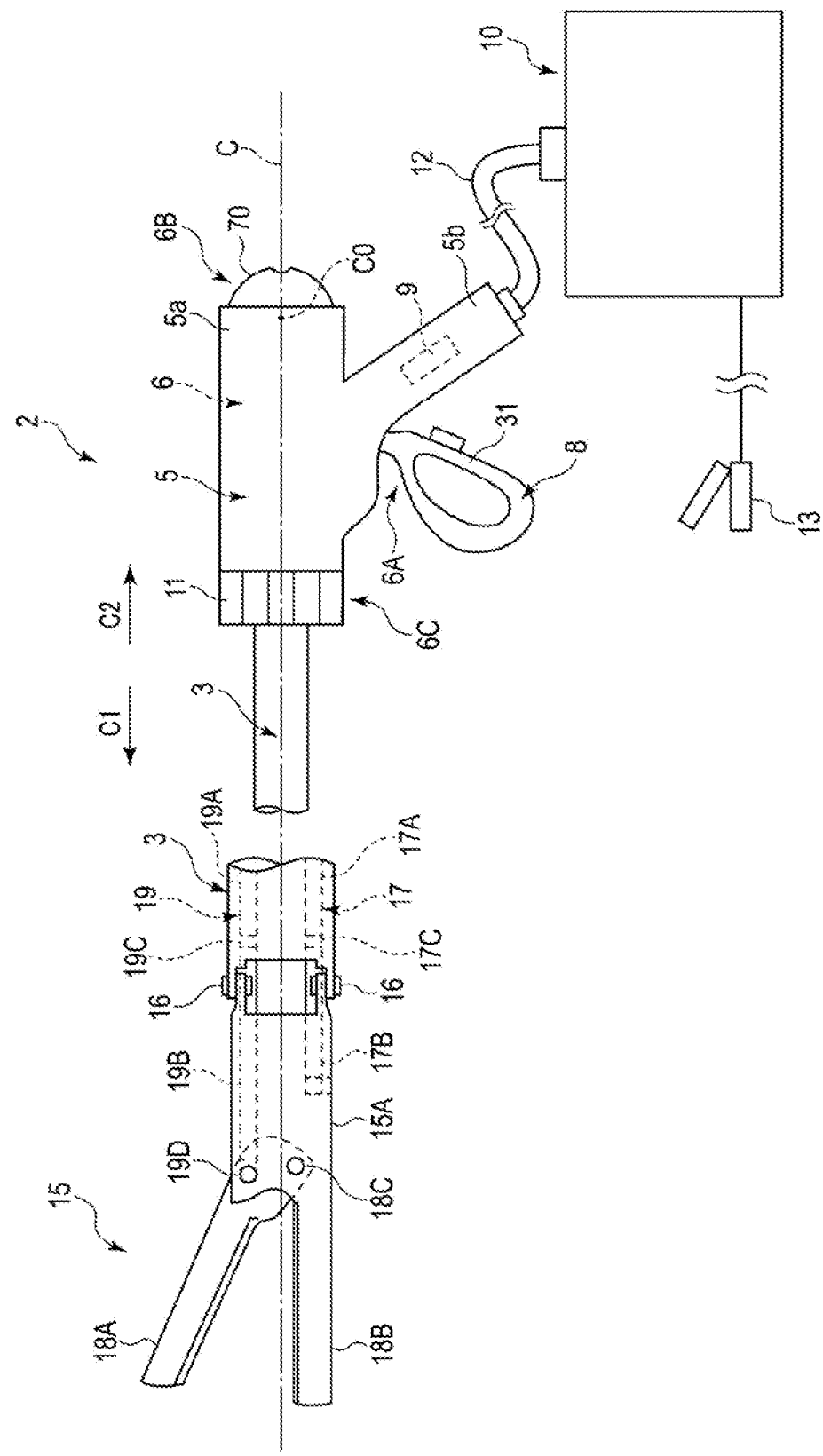
FIG. 1 is a schematic view illustrating a treatment system according to a first embodiment and also illustrating at an enlarged scale an end effector of a treatment tool of the treatment system and parts in the vicinity of the end effector.
Figure 2:
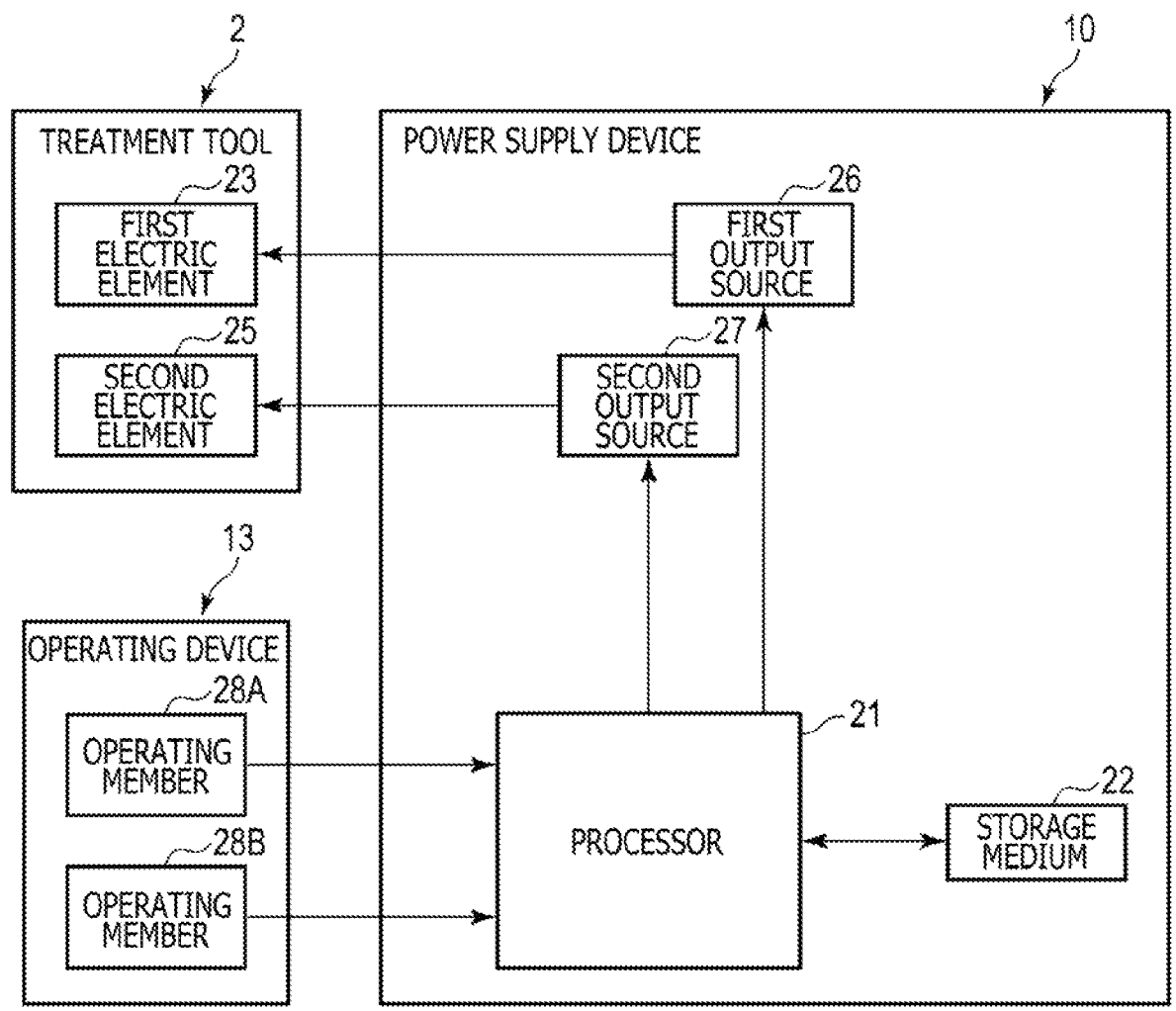
FIG. 2 is a schematic block diagram of the treatment system according to the first embodiment.
Figure 3A:
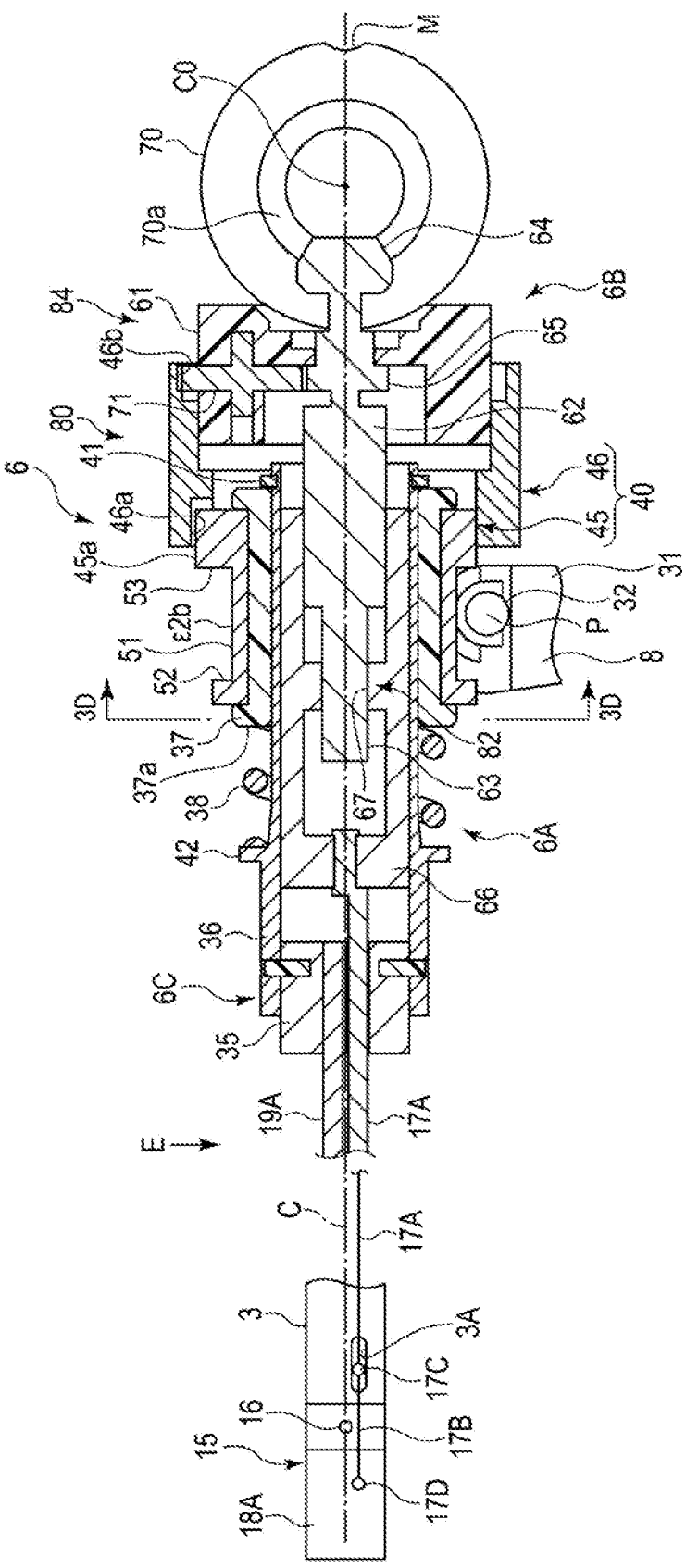
FIG. 3A is a schematic view illustrating a cross section of an actuating mechanism disposed in a housing of the treatment tool of the treatment system according to the first embodiment and also illustrating a state, or a neutral position, of the end effector with respect to the actuating mechanism, as viewed from a direction of an arrow E in an area illustrated in cross section.
Figure 3C:
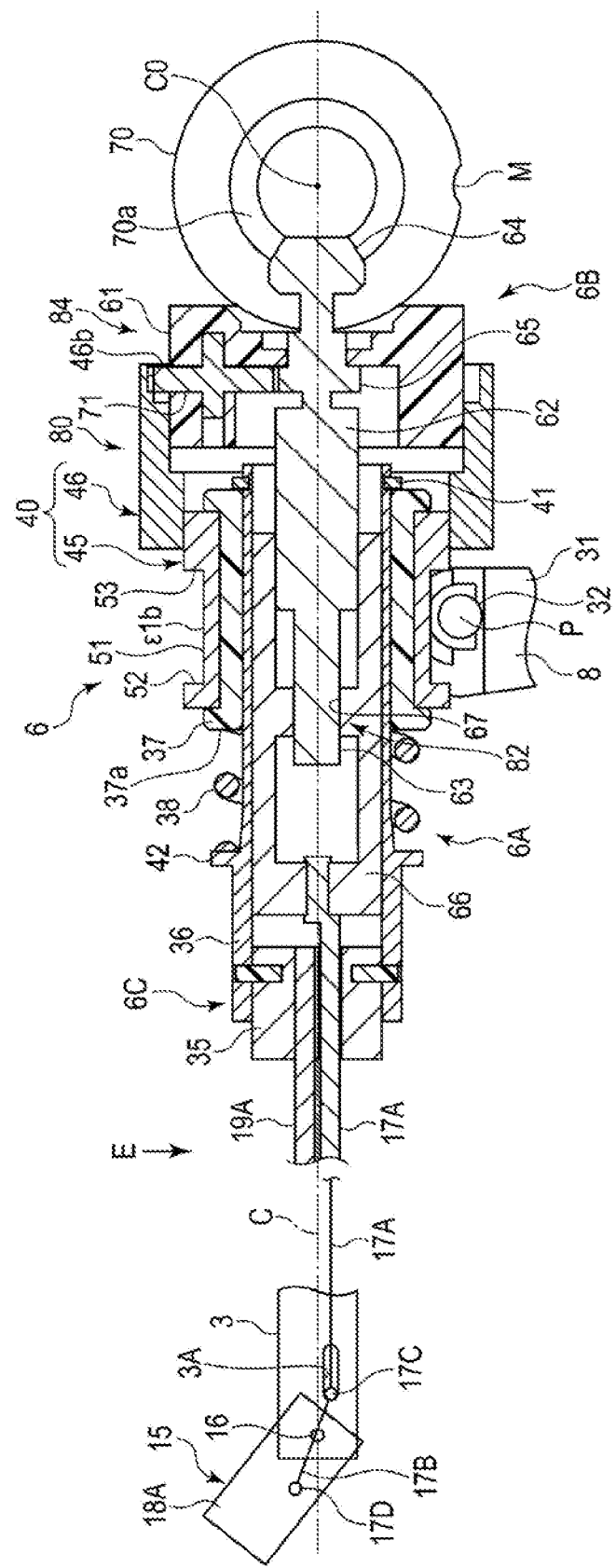
FIG. 3C is a schematic view illustrating the cross section of the actuating mechanism disposed in the housing of the treatment tool of the treatment system according to the first embodiment and also illustrating a state, or a second bent position, of the end effector with respect to the actuating mechanism, as viewed from a direction of an arrow E in an area illustrated in cross section.
Figure 3D:
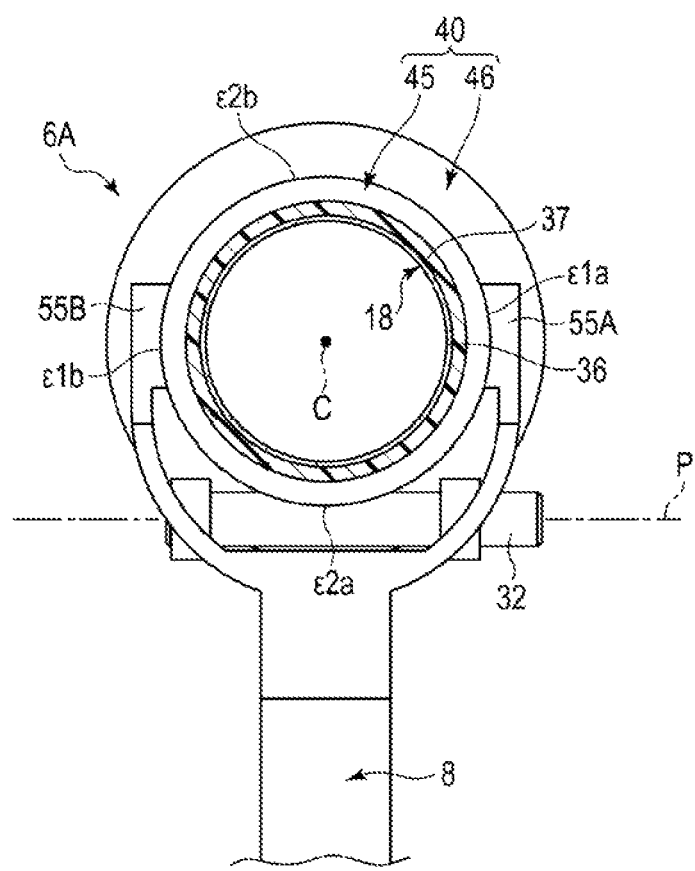
FIG. 3D is a schematic cross-sectional view taken along line 3D-3D of FIG. 3A, where a bending mechanism of the actuating mechanism is omitted from illustration.
Figure 4A:
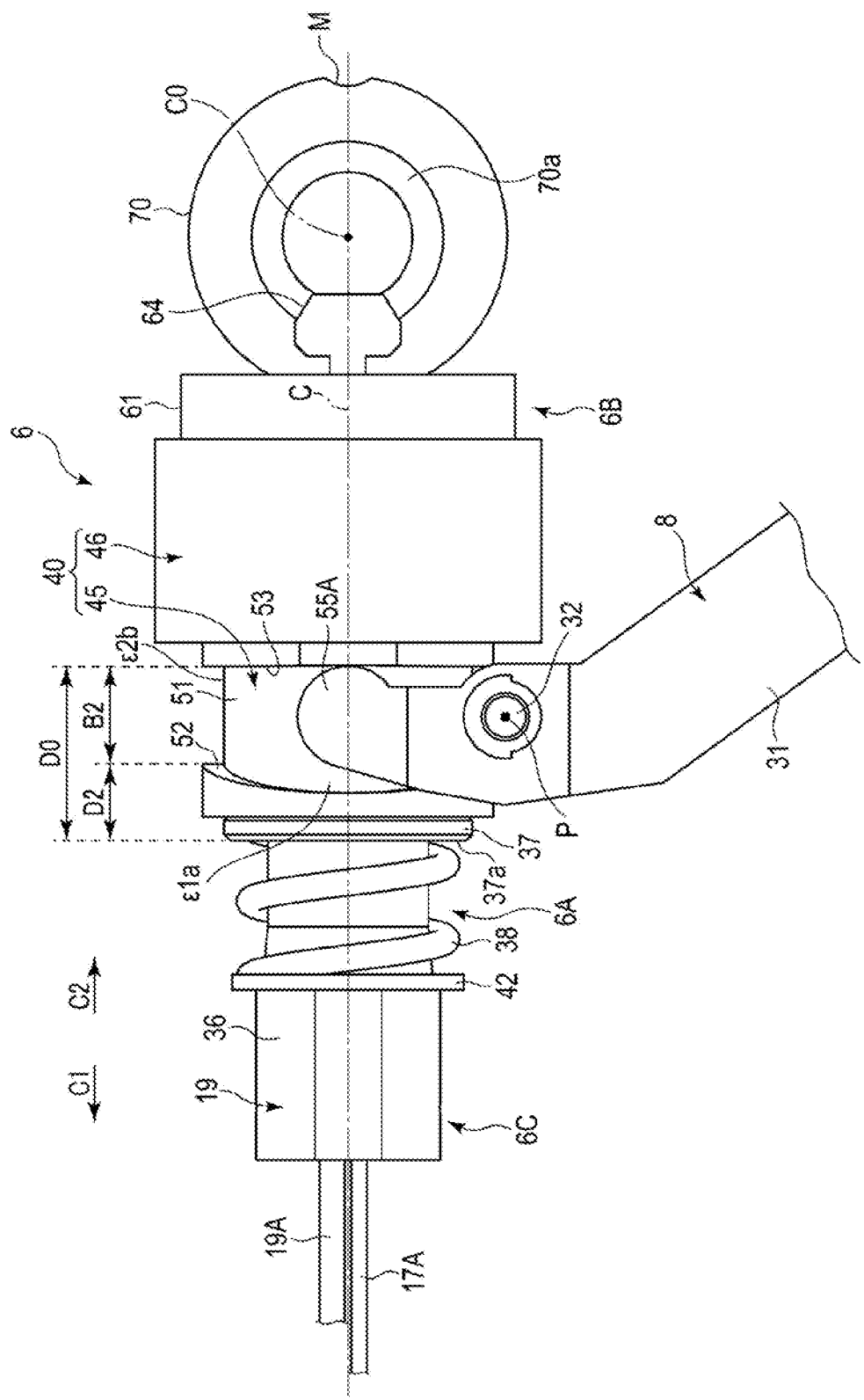
FIG. 4A is a schematic view illustrating the actuating mechanism disposed in the housing in a case where the end effector of the treatment tool of the treatment system according to the first embodiment is in the neutral position.
Figure 4B:
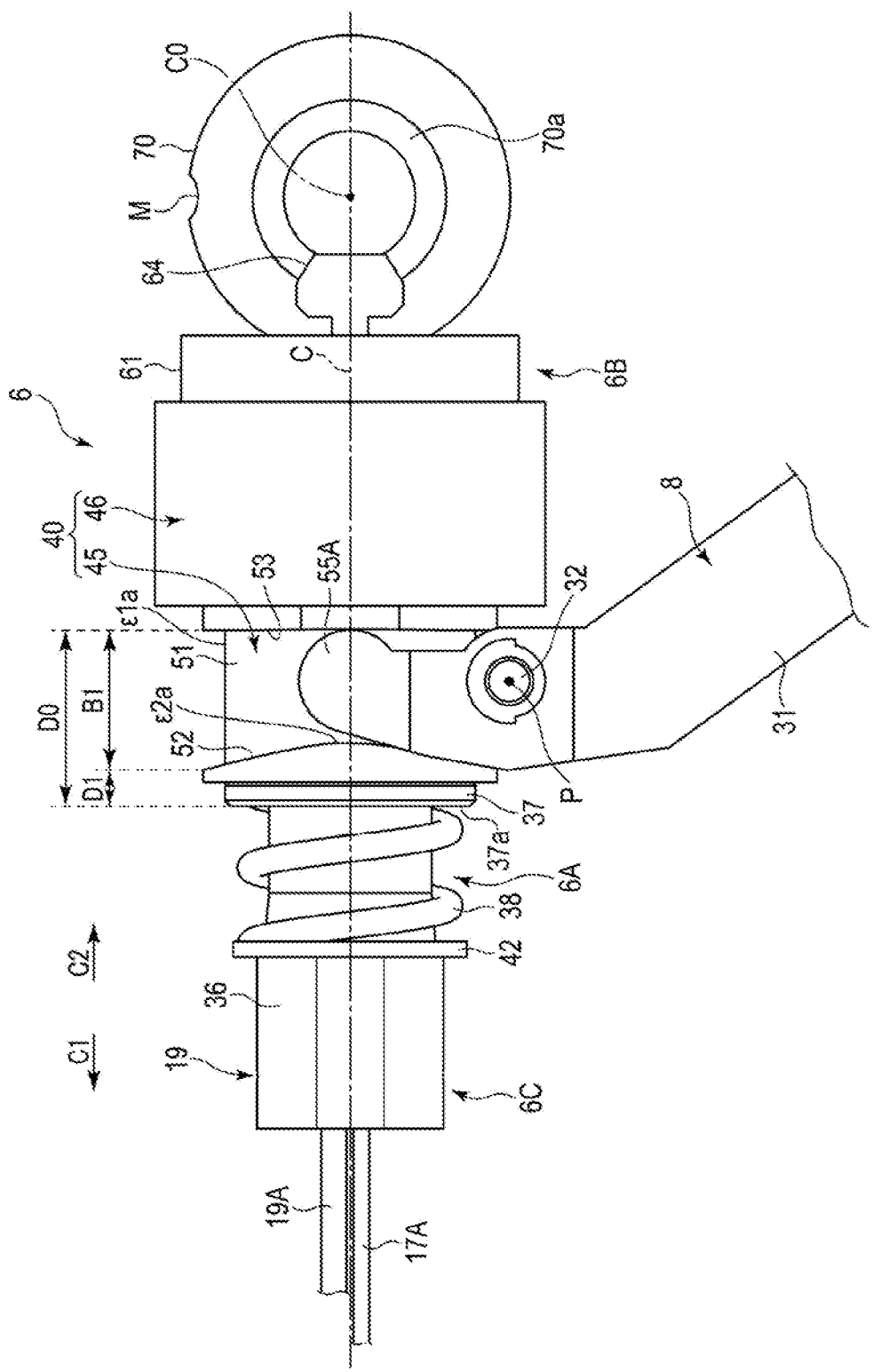
FIG. 4B is a schematic view illustrating the actuating mechanism disposed in the housing in a case where the end effector of the treatment tool of the treatment system according to the first embodiment is in a bent position.

FIG. 1 is a view illustrating a makeup of a treatment system using a treatment tool 2 according to the present embodiment. FIG. 2 is a diagram illustrating an arrangement for supplying electric energy to the treatment tool 2. FIGS. 3A through 3C are views illustrating the corresponding relationship between the position of an operating member 70 and the position of an end effector 15 with respect to the distal end of a sheath 3, with a housing 5 being omitted from illustration. FIG. 3D illustrates a cross section substantially parallel to the widthwise directions of the housing 5, where a bending mechanism 6B in a tubular member 36 of an opening and closing mechanism 6A is omitted from illustration. FIGS. 4A and 4B are views illustrating a state as viewed from one of the widthwise directions of the housing 5, particularly illustrating the corresponding relationship between the positions of the operating member 70 and the circumferential positions of a rotor assembly 40 with respect to a longitudinal axis C of a first member 45.

As illustrated in FIG. 1, the treatment tool 2 as a medical instrument includes the sheath 3. The sheath 3 has a substantially straight longitudinal axis C as a central axis and extends along the longitudinal axis C. Here, one side pointed by one of the directions along the longitudinal axis C is referred to as a distal-end side, or an arrow C1 side, and an opposite side to the distal-end side as a proximal-end side, or an arrow C2 side.

A housing 5 includes a main housing body 5a extending along the longitudinal axis C substantially coaxially therewith and a grip 5b, or a fixed handle, extending from the main housing body 5a in a direction transverse to the longitudinal axis C. The sheath is attached to the housing from its distal-end side. Further, as shown in FIG. 1, an end effector 15 is provided on the distal end side of the sheath 3 extending along the longitudinal axis C.

The housing 5 houses therein an actuating mechanism 6, or an actuating assembly, actuating the end effector 15 to be described hereinafter. In the present embodiment, the actuating mechanism 6 has an opening and closing mechanism 6A transmitting an actuating force, or an axial force, for opening and closing a pair of grasps 18A and 18B, to be described hereinafter, of the end effector 15 relatively to each other, to a first drive shaft 19 to be described hereinafter. The actuating mechanism 6 has a bending mechanism 6B moving the end effector 15 with respect to a distal end of the sheath 3 between a neutral position (see FIG. 3A) extending along the longitudinal axis C and a bent position (see FIGS. 3B and 3C) off the longitudinal axis C. The bending mechanism 6B is thus able to move the end effector 15 between a first bent position illustrated in FIG. 3B and a second bent position illustrated in FIG. 3C. The actuating mechanism 6 has a rotating mechanism 6C rotating the end effector 15 about the longitudinal axis C of the sheath 3. The actuating mechanism 6 includes parts shared by a plurality of kinds of mechanisms including the opening and closing mechanism 6A, the bending mechanism 6B, and the rotating mechanism 6C.

The opening and closing mechanism 6A has a handle 8, or a movable handle. The handle 8 is angularly movably attached to the housing 5. When the handle 8 is moved angularly with respect to the housing 5, the handle 8 is opened away from or closed toward the grip 5b. The grip 5b houses a stopper 9 therein. When the handle 8 is fully closed with respect to the grip 5b, the handle 8 abuts against the stopper 9. In the present embodiment, the handle 8 is positioned on one side of the longitudinal axis C where the grip 5b is positioned and on a distal-end side of the grip 5b. When the handle 8 is opened and closed, it is moved in directions substantially parallel to the longitudinal axis C. However, the disclosed technology is not limited such details. In an embodiment, the handle 8 is positioned on a proximal-end side of the grip 5b. In another embodiment, the handle 8 is positioned on a side of the longitudinal axis C which is opposite the side thereof where the grip 5b is positioned, and when the handle 8 is opened and closed, it is moved in directions substantially perpendicular to the longitudinal axis C.

In the embodiment illustrated in FIG. 1, the rotating mechanism 6C has a rotary knob 11, or a rotary operating member. The rotary knob 11, or the rotary operating member, is mounted on the housing 5. The rotary knob 11 is disposed substantially coaxially with the longitudinal axis C. When the rotary knob 11 is rotated about the longitudinal axis C, the sheath 3 rotates in unison with the rotary knob 11 about the longitudinal axis C with respect to the housing 5. In an embodiment, the rotary knob 11 may be dispensed with, and the sheath 3 may by non-rotatable about the longitudinal axis C with respect to the housing 5. Therefore, the rotating mechanism 6C is not necessarily required to be included.

A cable 12 has an end connected to the housing 5. The other end of the cable 12 is removably connected to a power supply device 10, or a control device. The treatment system 1 also includes an operating device 13. The operating device 13 receives an operation input that is entered to supply electric energy from the power supply device 10 to the treatment tool 2. In the embodiment illustrated in FIG. 1, a foot switch that is separate from the treatment tool 2 is included as the operating device 13. The foot switch is electrically connected to the power supply device 10. In another embodiment, an operating button or the like mounted on the housing 5, instead of or in addition to the foot switch, is included as the operating device 13.

The end effector 15 is mounted on the distal-end portion of the sheath 3. The end effector 15 includes a base body 15A. The base body 15A of the end effector 15 is angularly movable with respect to the distal end of the sheath 3 in a predetermined range by turning shafts 16 that extend perpendicularly to the longitudinal axis C, for example. The base body 15A and the turning shafts 16 are used as a direction changer for changing a position of a distal end of the end effector 15 from a position along the longitudinal axis C to a position off the position along the longitudinal axis C, with respect to the distal end of the sheath 3.

The bending mechanism 6B has a second drive shaft 17 extends along the longitudinal axis C. The second drive shaft 17 is moved when the end effector 15 is bent with respect to the distal end of the sheath 3 by the base body 15A and the turning shafts 16 that function as the direction changer. In the present embodiment, of the bending mechanism 6B, a flexing mechanism flexing the end effector 15 with respect to the distal end of the sheath 3 will hereinafter be described. The second drive shaft 17 has a first link 17A, or a first rod, and a second link 17B, or a second rod, for example. The first link 17A is movable in a predetermined range along the longitudinal axis C of the sheath 3, for example. The sheath 3 has an oblong hole 3A defined therein in the vicinity of the distal-end portion thereof and receiving therein a support shaft 17C that interconnects a distal end of the first link 17A and a proximal end of the second link 17B. The support shaft 17C extends parallel to the turning shafts 16. The oblong hole 3A defines an interval in which the support shaft 17C is movable. The position of the oblong hole 3A, i.e., the distal end of the first link 17A, is offset from the turning shafts 16 in the circumferential directions of the sheath 3. The second link 17B is coupled to the distal-end side of the first link 17A and supported by the end effector 15. The second link 17B has a distal end 17D whose position with respect to the base body 15A of the end effector 15 remains unchanged.

In a case where the support shaft 17C is located substantially around the center between the distal and proximal ends of the oblong hole 3A along the longitudinal axis C, the end effector 15 is in the neutral position in which it extends straight along the longitudinal axis C of the sheath 3, as illustrated FIG. 3A. When the first link 17A moves toward the proximal-end side along the longitudinal axis C, the distal end 17D of the second link 17B tends to move the end effector 15 toward the proximal-end side. In this case, the end effector 15 is bent to a state illustrated in FIG. 3B, for example, or a first bent position, about the turning shafts 16 with respect to the distal end of the sheath 3. When the first link 17A moves toward the distal-end side along the longitudinal axis C, the distal end 17D of the second link 17B tends to move the end effector 15 toward the distal-end side. In this case, the end effector 15 is bent to a state illustrated in FIG. 3C, for example, or a second bent position, about the turning shafts 16 with respect to the distal end of the sheath 3. An angle through which the end effector 15 is bent from the neutral position to the first bent position can be set to an appropriate value. An angle through which the end effector 15 is bent from the neutral position to the second bent position can be set to an appropriate value.

The end effector 15 includes a pair of grasps 18A and 18B, or clamp members. The pair of grasps 18A and 18B, or the clamp members, is disposed on a distal-end side of the base body 15A. At least one of the grasps 18A and 18B is angularly movable with respect to the base body 15A by a turning shaft 18C perpendicular to the longitudinal axis C. The grasps 18A and 18B are openable and closable relatively to each other. Therefore, the end effector 15 is able to grip a treatment target such as a biotissue or the like between the grasps 18A, 18B. In an embodiment, one of the grasps 18A and 18B, e.g., the second grasp 18B, is fixedly mounted on the base body 15A, whereas the other of the grasps 18A and 18B, e.g., the first grasp 18A, is angularly movably mounted on the base body 15A. In another embodiment, both of the grasps 18A and 18B are angularly movably mounted on the base body 15A.

The opening and closing mechanism 6A has a first drive shaft 19 extending along the longitudinal axis C. The first drive shaft 19 is moved when the pair of grasps 18A and 18B, or clamp members, is to be opened or closed relatively to each other. The first drive shaft 19 is movable along the longitudinal axis C with respect to the sheath 3. The first drive shaft 19 has a first link 19A, or a first rod, and a second link 19B, or a second rod. The first link 19A is movable along the longitudinal axis C of the sheath 3, for example. A distal end of the first link 19A and a proximal end of the second link 19B are interconnected by a support shaft 19C. The support shaft 19C should preferably extend perpendicularly to the longitudinal axis C and parallel to the support shaft 17C on the second drive shaft 17 of the bending mechanism 6B. The support shaft 19C is disposed in the vicinity of the distal-end portion of the sheath 3. The second link 19B is coupled to the distal-end side of the first link 19A and supported on the first grasp 18A by a joint shaft 19D. The joint shaft 19D should preferably extend parallel to the turning shaft 18C.

The first drive shaft 19 is inserted into the housing 5 from the distal-end side thereof. The first link 19A of the first drive shaft 19 has a proximal-end portion that supports a slider 37 within the main housing body 5a, i.e., within the housing 5. The slider 37 is movable with respect to the first drive shaft 19. In the embodiment that includes the rotary knob 11, the first drive shaft 19 and the end effector 15 are rotated in unison with the sheath 3 about the longitudinal axis C by rotating the rotary knob 11.

As illustrated in FIG. 2, the power supply device 10 includes a processor 21 and a storage medium 22. The processor 21 is constructed as an integrated circuit or the like that includes a CPU (Central Processing Unit), an ASIC (Application Specific Integrated Circuit), an FPGA (Field Programmable Gate Array), or the like. The power supply device 10 may include a single processor 21 or a plurality of processors 21. The processor 21 performs processing sequences according to programs stored in the processor 21 or the storage medium 22. The storage medium 22 stores processing programs that are used by the processor 21. The storage medium 22 also stores parameters, functions, tables, and the like that are used in arithmetic operations carried out by the processor 21. The processor 21 detects operation inputs entered in the operating device 13.

The treatment tool 2 includes a first electric element 23 and a second electric element 25. The power supply device 10 further includes a first output source 26 and a second output source 27. The first output source 26 includes a converting circuit or the like and converts electric power from a battery power supply, an outlet power supply, or the like into electric energy to be supplied to the first electric element 23. Then, the first output source 26 outputs the converted electric energy to the first electric element 23. The second output source 27 includes a converting circuit or the like and converts electric power from the battery power supply, the outlet power supply, or the like into electric energy to be supplied to the second electric element 25. Then, the second output source 27 outputs the converted electric energy to the second electric element 25. Each of the electric elements 23 and 25 is energized when supplied with the electric energy.

In an embodiment, the end effector 15 includes bipolar electrodes as the first electric element 23. In another embodiment, the end effector 15 includes a heater as the second electric element 25.

The processor 21 controls output of electric energy from the output sources 26 and 27 to control supply of electric energy to the electric elements 23 and 25, on the basis of operations on the operating device 13. The treatment target is thus appropriately treated.

As illustrated in FIG. 1, the handle 8 includes a protrusion 31 projecting out of the housing 5 from within the housing 5. An operating force for opening or closing the handle 8 with respect to the grip 5b is applied to the protrusion 31. The handle 8 includes a portion other than the protrusion 31 that is inserted in the housing 5. In the housing 5, the handle 8 is angularly movably supported on the housing 5 by a support pin 32. The support pin 32 has a central axis that functions as a turn axis P, or a turn center, about which the handle 8 is angularly movable. In the present embodiment, the turn axis P extends along the widthwise directions of the housing 5.

The housing 5 houses therein part of the opening and closing mechanism 6A of the actuating mechanism 6. In the present embodiment, the opening and closing mechanism 6A has the first drive shaft 19, the slider 37, or a first slider, that is of a tubular shape, a tubular resilient member 38 such as a helical spring, and the rotor assembly 40 that is of a tubular shape.

The first link 19A of the first drive shaft 19, or the drive shaft, extends from within the housing 5 through the sheath 3. The first drive shaft 19 further includes a relay member 35 to which the proximal end of the first link 19A is connected or fixed and a tubular member 36 mounted on a proximal-end portion of the relay member 35. The relay member 35 and the tubular member 36 are disposed in the main housing body 5a. The tubular member 36 has a central axis coaxial or substantially coaxial with the longitudinal axis C of the sheath 3. The tubular member 36 extends from the relay member 35 toward the proximal-end side. The first link 19A, the relay member 35, and the tubular member 36 of the first drive shaft 19 move together along the longitudinal axis C with respect to the sheath 3 and the housing 5. In the present embodiment, the support pin 32 or the turn axis P is disposed between the protrusion 31 of the handle 8 and the tubular member 36.

The slider 37 is disposed on an outer circumferential surface of the tubular member 36 of the first drive shaft 19. The slider 37 has a central axis coaxial or substantially coaxial with the longitudinal axis C of the sheath 3. The slider 37 is movable along the longitudinal axis C with respect to the first drive shaft 19. A stopper 41 is disposed on an outer circumferential surface of the tubular member 36. The stopper 41 is disposed on a proximal-end side with respect to the slider 37 and fixed to the first drive shaft 19. When the slider 37 abuts against the stopper 41, the slider 37 is restrained from moving into an area on the proximal-end side of the stopper 41. In the present embodiment, furthermore, a ridge 42 that projects toward an outer circumferential side is disposed on the outer circumferential surface of the tubular member 36. The ridge 42 is, for example, integrally formed with the tubular member 36 and disposed on a distal-end side of the slider 37.

The resilient member 38 is disposed on an outer circumferential surface of the tubular member 36 of the first drive shaft 19. The resilient member 38 extends along the longitudinal axis C between the ridge 42 and the slider 37. The resilient member 38 has an end, or a distal end, held in contact with or connected to the ridge 42 of the first drive shaft 19. The resilient member 38 has another end, or a proximal end, held in contact with or connected to the slider 37. Therefore, the resilient member 38 is disposed between the first drive shaft 19 and the slider 37 in the directions along the longitudinal axis C. When the slider 37 is moved along the longitudinal axis C with respect to the first drive shaft 19, the resilient member 38 is expanded or compressed. Even when the slider 37 is in abutment against the stopper 41, i.e., when the slider 37 is most widely spaced from the ridge 42, the resilient member 38 is compressed from its natural length. Therefore, even when the slider 37 abuts against the stopper 41, a resilient force acts from the resilient member 38 on the first drive shaft 19 toward the distal-end side. When the slider 37 is moved out of abutment against the stopper 41 toward the distal-end side with respect to the first drive shaft 19, the resilient member 38 is further compressed between the slider 37 and the ridge 42 of the first drive shaft 19, increasing the resilient force acting from the resilient member 38 on the first drive shaft 19.

The rotor assembly 40 is mounted on the slider 37. The rotor assembly 40 has a central axis coaxial or substantially coaxial with the longitudinal axis C of the sheath 3. The rotor assembly 40 is rotatable about the longitudinal axis C with respect to the slider 37 and the first drive shaft 19. The rotor assembly 40 includes a first member 45, or a second slider, mounted on an outer circumferential surface of the slider 37 and a second member 46 mounted on a proximal-end portion of the first member 45. The members 45 and 46 of the rotor assembly 40 are jointly rotatable about the longitudinal axis C with respect to the slider 37. The first member 45 is movable along the longitudinal axis C with respect to the second member 46. The first member 45 is movable in unison with the slider 37 along the longitudinal axis C with respect to the second member 46 and the first drive shaft 19. In other words, the slider 37 and the first member 45 function as a slider assembly.

For example, in an embodiment, the first member 45 includes an engaging ledge 45a on an outer circumferential surface thereof, and the second member 46 includes an elongate engaging groove 46a defined in an inner circumferential surface thereof along the longitudinal axis C. The engaging ledge 45a of the first member 45 engages in the engaging groove 46a of the second member 46. In the engaging groove 46a, the engaging ledge 45a is movable along the longitudinal axis C, but is restrained from rotating about the longitudinal axis C. Therefore, the first member 45 is movable along the longitudinal axis C with respect to the second member 46, but is non-rotatable about the longitudinal axis C with respect to the second member 46.

The first member 45 of the rotor assembly 40 has a groove 51 defined in an outer circumferential surface thereof around the longitudinal axis C, the groove 51 being concave toward an inner circumferential side. In the present embodiment, the groove 51 is defined over the whole circumference around the longitudinal axis C. The groove 51 has a width B in the directions along the longitudinal axis C, the width B being different at angular positions about the longitudinal axis C. For example, at each of an angular position ε1a, or a first angular position, and an angular position ε1b, or a first angular position, that is substantially 180° spaced apart from the angular position 1a about the longitudinal axis C, the groove 51 has a first width B1 in the directions along the longitudinal axis C. Furthermore, at each of an angular position ε2a, i.e., a second angular position, that is substantially 90° spaced apart from the angular position ε1a about the longitudinal axis C and an angular position ε2b, i.e., a second angular position, that is substantially 180° spaced apart from the angular position ε2a about the longitudinal axis C, the groove 51 has a second width B2 smaller than the first width B1 in the directions along the longitudinal axis C. In the present embodiment, the groove 51 is of a symmetrical shape around the longitudinal axis C.

In the present embodiment, in a range from the angular position ε1a, or the first angular position, to the angular position ε2a, or the second angular position, around the longitudinal axis C, the width B of the groove 51 decreases continuously from the first width B1 to the second width B2. Similarly, in a range from the angular position ε1b, i.e., the first angular position, to the angular position ε2b, i.e., the second angular position, around the longitudinal axis C, the width B of the groove 51 decreases continuously from the first width B1 to the second width B2.

However, in the range from the angular position ε1a, or the first angular position, to the angular position ε2a, or the second angular position, around the longitudinal axis C, the width B of the groove 51 may decrease stepwise from the first width B1 to the second width B2. Similarly, in the range from the angular position ε1b, or the first angular position, to the angular position ε2b, or the second angular position, around the longitudinal axis C, the width B of the groove 51 may decrease stepwise from the first width B1 to the second width B2.

The groove 51 has a first groove side face 52 and a second groove side face 53. The second groove side face 53 is spaced more away from the resilient member 38 than the first groove side face 52 in a direction along the longitudinal axis C. In the present embodiment, the second groove side face 53 is positioned on a proximal-end side of the first groove side face 52. The dimension between the groove side faces 52 and 53 in the direction along the longitudinal axis C represents the width B of the groove 51.

At each of the angular positions εa and ε1b, or the first angular positions, about the longitudinal axis C, the first groove side face 52 is spaced a first distance D1 from an end 37a of the resilient member 38 that is closer to the slider 37, or the position where the resilient member 38 is held in contact with or connected to the slider 37, i.e., from the proximal end of the resilient member 38 in the present embodiment, in the directions along the longitudinal axis C. In addition, at each of the angular positions ε2a and ε2b, or the second angular positions, about the longitudinal axis C, the first groove side face 52 is spaced a second distance D2 that is larger than the first distance D1 from the end 37a of the resilient member 38 that is closer to the slider 37, i.e., from the proximal end of the resilient member 38 in the present embodiment, in the directions along the longitudinal axis C. At any of the angular positions about the longitudinal axis C, the end 37a of the resilient member 38 that is closer to the slider 37 is spaced from the second groove side face 53 by a uniform distance D0 in the directions along the longitudinal axis C. Therefore, the second width B2 of the groove 51 at each of the angular positions ε2a and ε2b, or the second angular positions, is smaller than the first width B1 of the groove 51 at each of the angular positions ε1a and ε1b, or the first angular positions.

The handle 8 includes a pair of engaging portions 55A and 55B on a side thereof that is opposite the protrusion 31 across the support pin 32 or the turn axis P. Each of the engaging portions 55A and 55B is inserted in the groove 51 of the rotor assembly 40 and engages in the groove 51. With each of the engaging portions 55A and 55B engaging in the groove 51, the handle 8 is mounted on the first member 45 of the rotor assembly 40. The rotor assembly 40 is rotatable about the longitudinal axis C with respect to the handle 8. Upon rotation of the rotor assembly 40 about the longitudinal axis C, the position where the engaging portion 55A engages in the groove 51 changes between the angular position ε1a, or the first angular position, and the angular position ε2a, or the second angular position. Furthermore, the position where the engaging portion 55A engages in the groove 51 changes between the angular position ε1a, or the first angular position, and the angular position ε2b, or the second angular position. Similarly, upon rotation of the rotor assembly 40 about the longitudinal axis C, the position where the engaging portion 55B engages in the groove 51 changes between the angular position ε1b, or the first angular position, and the angular position ε2b, or the second angular position. Furthermore, the position where the engaging portion 55B engages in the groove 51 changes between the angular position ε1b, or the first angular position, and the angular position ε2a, or the second angular position.

When the handle 8 is most widely opened from the grip 5b, each of the engaging portions 55A and 55B abuts against the second groove side face 53 in the groove 51 from the distal-end side, and is spaced from the first groove side face 52 toward the proximal-end side. When the handle 8 is most widely opened from the grip 5b, the slider 37 abuts against the stopper 41. For gripping a treatment target between the grasps 18A and 18B, the treatment target is placed between the grasps 18A and 18B while the handle 8 is being most widely opened from the grip 5b, and then the handle 8 is closed toward the grip 5b. Each of the engaging portions 55A and 55B in the groove 51 is now moved about the support pin 32 toward the first groove side face 52 in a direction toward the distal-end side, and is brought into abutment against the first groove side face 52 from the proximal-end side.

As each of the engaging portions 55A and 55B abuts against the first groove side face 52, each of the engaging portions 55A and 55B presses the first groove side face 52 toward the distal-end side, transmitting a pressing force through the first member 45 of the rotor assembly 40, the slider 37, and the resilient member 38 to the first drive shaft 19. The first drive shaft 19 is thus moved together with the first member 45, the slider 37, and the resilient member 38 toward the distal-end side with respect to the housing 5 and the sheath 3. As the first drive shaft 19 is moved toward the distal-end side, the joint shaft 19D on the distal end of the first drive shaft 19 is moved toward the distal-end side, whereupon at least one of the grasps 18A and 18B is moved angularly with respect to the base body 15A, closing the grasps 18A and 18B relatively to each other. At this time, the grasp 18A and/or the grasp 18B is moved angularly until the treatment target therebetween is compressed to a certain extent, and the grasps 18A and 18B are closed relatively to each other until the treatment target therebetween is compressed to a certain extent.

When the gripped treatment target is compressed to a certain extent, the grasp 18A and/or the grasp 18B stops being moved angularly, and the first drive shaft 19 also stops being moved toward the distal-end side with respect to the housing 5 and the sheath 3.

Then, when the handle 8 is closed with respect to the grip 5b until the handle 8 abuts against the stopper 9, the pressing force from each of the engaging portions 55A and 55B is transmitted through the first member 45 to the slider 37, which is moved toward the distal-end side with respect to the first drive shaft 19. As a result, the resilient member 38 is compressed, increasing the resilient force that acts from the resilient member 38 on the first drive shaft 19 toward the distal-end side. As the resilient force from the resilient member 38 to the first drive shaft 19 is increased, the griping force applied to the treatment target between the grasps 18A and 18B is increased.

As illustrated in FIGS. 3A through 3C, the end effector 15 can change to the neutral position, or a first state, in which the end effector 15 extends along the longitudinal axis C of the sheath 3 with respect to the distal end of the sheath 3, and to the bent position, or a second state, off the longitudinal axis C of the sheath 3. In the bent position, the end effector 15 is bent about the turning shafts 16 with respect to the distal end of the sheath 3. At this time, the end effector 15 is bent to a state illustrated in FIG. 3B and a state illustrated in FIG. 3C with respect to the distal end of the sheath 3.

The actuating mechanism 6 of the present embodiment includes the opening and closing mechanism 6A and the bending mechanism 6B that are operatively linked with each other. The bending mechanism 6B is disposed in the first drive shaft 19 and in the second member 46 of the rotor assembly 40.

The bending mechanism 6B has a tubular support body 61 and a main rotational shaft 62, or a rotational shaft, disposed in the support body 61. The main rotational shaft 62 has a central axis that should preferably be disposed coaxially or substantially coaxially with the longitudinal axis C of the sheath 3. The main rotational shaft 62 is rotatable about the longitudinal axis C with respect to the housing 5. The main rotational shaft 62 has a first gear 63 on an outer circumferential surface of a distal-end portion thereof. The first gear 63 may be in the form of an externally threaded gear, for example. The main rotational shaft 62 has a second gear 64 on a proximal-end portion thereof. The second gear 64 may be in the form of a bevel gear, a crown gear, or the like, for example. The main rotational shaft 62 has a third gear 65 positioned closer to the proximal-end side than the proximal end of the first drive shaft 19. The third gear 65 is in the form of a spur gear, for example.

A second slider 66 is disposed in the tubular member 36 of the first drive shaft 19. The second slider 66 is movable along the longitudinal axis C relatively to the tubular member 36 and is rotatable about the longitudinal axis C. The second slider 66 has an internal gear 67 on an inner circumferential surface thereof that is held in mesh with the first gear 63. The internal gear 67 is in the form of an internally threaded gear, for example. In the present embodiment, the first link 17A of the second drive shaft 17 that contributes to the bending of the end effector 15 with respect to the distal end of the sheath 3 is disposed on the longitudinal axis C, or a central axis, of the slider 66. The first link 17A extends through the relay member 35. In the present embodiment, the first link 17A extends through the relay member 35 at a position parallel to and offset from the central axis C. The first link 17A has a proximal-end portion supported on the second slider 66 such that the first link 17A is moved along the longitudinal axis C as the second slider 66 is moved along the longitudinal axis C. The proximal-end portion of the first link 17A is rotatably supported on the second slider 66 by a bearing, not illustrated, on the longitudinal axis C for rotation about the longitudinal axis C. Therefore, when the first link 17A is rotated about the longitudinal axis C, the second slider 66 is not rotated about the longitudinal axis C.

In the present embodiment, the operating member 70, or a control member, is rotatably supported on the support body 61 for rotation about a rotational axis C0 perpendicular to the longitudinal axis C. The operating member 70 is in the form of a dial rotatable about the rotational axis C0. The operating member 70 has a gear 70a meshing with the second gear 64. The gear 70a may be in the form of a bevel gear, a crown gear, or the like, for example.

A rotary gear 71 is supported in the support body 61. The rotary gear 71 is in the form of a spur gear, for example. The rotary gear 71 is held in mesh with a third gear 65 of the main rotational shaft 62 and also with a gear 46b, or a circumferential gear, on an inner circumferential surface of the second member 46 of the rotor assembly 40.

Consequently, when the operating member 70 is rotated, since the second gear 64 is rotated about the longitudinal axis C by the gear 70a, the main rotational shaft 62 is rotated. The rotation of the main rotational shaft 62 causes the second slider 66 to move along the longitudinal axis C. Therefore, the second gear 64 and the first gear 63 and the internal gear 67 of the main rotational shaft 62 function as a gear assembly 82 that moves the second slider 66 along the longitudinal axis C upon rotation of the operating member 70 and the main rotational shaft 62. The rotation of the operating member 70 and the main rotational shaft 62 causes the second member 46 of the rotor assembly 40 disposed outwardly of the rotary gear 71 to rotate. Therefore, the second gear 64, the third gear 65 of the main rotational shaft 62, the rotary gear 71, and the circumferential gear 46b function as a gear assembly 84 that rotates the second member 46 of the rotor assembly 40 about the longitudinal axis C. The rotation of the second member 46 of the rotor assembly 40 causes the first member 45 to rotate about the longitudinal axis C in unison with the second member 46. Accordingly, the circumferential position of the groove 51 with respect to the pair of engaging portions 55A and 55B is changed depending on the rotation of the operating member 70.

In response to the operation of the operating member 70, therefore, the rotation of the rotor assembly 40 of the opening and closing mechanism 6A about the longitudinal axis C and the movement of the second drive shaft 17 of the bending mechanism 6B along the longitudinal axis C are interlinked. Consequently, the gear assembly 82, the second slider 66, the gear assembly 84, and the rotor assembly 40 are used as an adjusting mechanism 80 adjusting a movable range of the slider 37 with respect to the first drive shaft 19. Specifically, the adjusting mechanism 80 adjusts the movable range of the slider 37 with respect to the first drive shaft 19 depending on a position of a mark M on the operating member 70, or an operated state thereof.

By way of example, when the mark M on the operating member 70 is in the position illustrated in FIG. 3A, the end effector 15 is in the neutral position. When the mark M on the operating member 70 is in the position illustrated in FIG.

3B, the end effector 15 is in the first bent position. When the mark M on the operating member 70 is in the position illustrated in FIG. 3C, the end effector 15 is in the second bent position. When the mark M on the operating member 70 is off the position illustrated in FIG. 3A, the end effector 15 is bent with respect to the distal end of the sheath 3.

Next, operation of the treatment system 1 according to the present embodiment will be described.

A state in which the engaging portion 55A engages in the groove 51 at the angular position ε1a, i.e., the first angular position, and the engaging portion 55B engages in the groove 51 at the angular position ε1b, or the first angular position, is referred to as a first engaging state. A state in which the engaging portion 55A engages in the groove 51 at the angular position ε2a, or the second angular position, and the engaging portion 55B engages in the groove 51 at the angular position ε2b, or the second angular position, is referred to as a second engaging state. A state in which the engaging portion 55A engages in the groove 51 at the angular position ε2b, or the second angular position, and the engaging portion 55B engages in the groove 51 at the angular position ε2a, or the second angular position, is referred to as a third engaging state.

In FIGS. 3A and 4A, the engaging portions 55A and 55B engage in the groove 51 in the first engaging state. In FIGS. 3B and 4B, the engaging portions 55A and 55B engage in the groove 51 in the second engaging state. In FIG. 3C, the engaging portions 55A and 55B engage in the groove 51 in the third engaging state. As described hereinbefore, the second width B2 of the groove 51 in each of the angular positions ε2a and ε2b, or the second angular positions, is smaller than the first width B1 of the groove 51 in each of the angular positions ε1a and ε1b, or the first angular positions. Therefore, the distance that the handle 8 moves from its most widely opened position until each of the engaging portions 55A and 55B abuts against the first groove side face 52 is smaller in the second engaging state and the third engaging state than in the first engaging state. In the present embodiment, the range in which the handle 8 moves from its most widely opened position toward the grip 5b until the handle 8 abuts against the stopper 9 remains unchanged.

When the handle 8 is closed, the first drive shaft 19 starts moving toward the distal-end side through the slider assembly, or the slider 37 and the first member 45, earlier in the second engaging state and the third engaging state than in the first engaging state. Providing other conditions such as the size of the treatment target to be gripped are the same, the slider assembly starts moving with respect to the first drive shaft 19, and the resilient member 38 starts to be compressed, earlier in the second engaging state and the third engaging state than in the first engaging state. Therefore, the distance that the resilient member 38 is compressed at the time the handle 8 abuts against the stopper 9 is larger in the second engaging state and the third engaging state than in the first engaging state. Thus, the resilient force transmitted from the resilient member 38 to the first drive shaft 19 is larger in the second engaging state and the third engaging state than in the first engaging state. Consequently, an axial force F transmitted to the first link 19A is larger in the second engaging state and the third engaging state than in the first engaging state.

When the rotary knob 11 of the rotating mechanism 6C is rotated about the longitudinal axis C with respect to the housing 5, the tubular member 36, the relay member 35, and the first link 19A are rotated in unison with the sheath 3 about the longitudinal axis C. Therefore, the end effector 15 is also rotated in unison with the sheath 3 about the longitudinal axis C. Meanwhile, the first link 17A is supported on the second slider 66 at the longitudinal axis C. Therefore, when the rotary knob 11 is rotated about the longitudinal axis C, rotating the first link 17A in unison with the first drive shaft 19 about the longitudinal axis C, the slider 66 disposed in the tubular member 36 is not rotated with respect to the tubular member 36. In addition, the main rotational shaft 62 coupled to the second slider 66, the support body 61, the rotor assembly 40, and the operating member 70 are not rotated in unison with the first drive shaft 19, the slider 37, and the like about the longitudinal axis C.

In a case where an angular position of the operating member 70 of the bending mechanism 6B with respect to the rotational axis C0 is the position illustrated in FIG. 3A with respect to the housing 5, the end effector 15 is in the neutral position in which it extends along the longitudinal axis C toward the distal-end side with respect to the distal end of the sheath 3. At this time, the engaging portions 55A and 55B engage in the groove 51 in the first engaging state described hereinbefore in which the engaging portion 55A engages in the groove 51 at the angular position ε1a, or the first angular position, and the engaging portion 55B engages in the groove 51 at the angular position ε1b, or the first angular position.

Figure 5A:
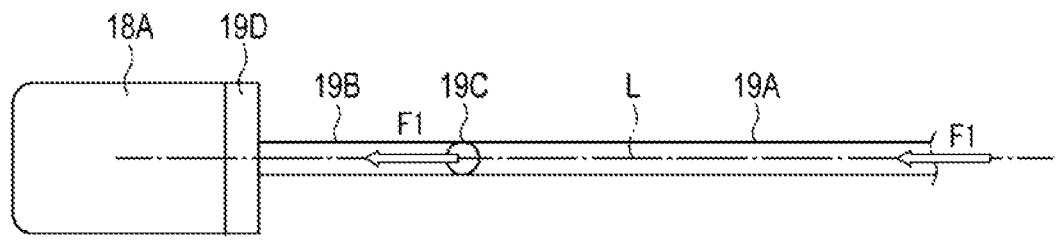
FIG. 5A is a schematic view illustrating an axial force transmitted to a first drive shaft disposed in the housing and a sheath at the time an opening and closing mechanism of the actuating mechanism is operated while the end effector of the treatment tool of the treatment system according to the first embodiment is in the neutral position.

The handle 8 of the opening and closing mechanism 6A is closed toward the grip 5b and moved until it abuts against the stopper 9. At this time, as illustrated in FIG. 5A, the axial force F is transmitted successively to the first link 19A and the second link 19B in the order named, pushing the joint shaft 19D, i.e., the first grasp 18A, along the longitudinal axis C toward the distal-end side thereby to grip the treatment target between the grasps 18A and 18B. If it is assumed that the first link 19A and the second link 19B are rigid bodies and the support shaft 19C transmits the force from the first link 19A to the second link 19B without loss, an axial force F1 applied to the proximal end of the first link 19A is applied as it is to the second link 19B. A maximum gripping force that is exerted between the pair of grasps 18A and 18B at this time is referred to as a first gripping force.

When the surgeon enters an operation input through the operating device 13 while the treatment target is being gripped, the power supply device 10 supplies electric energy to the treatment tool 2. As described hereinbefore, treatment energy is therefore applied to the treatment target, treating the gripped treatment target.

After applying the treatment energy to the gripped treatment target, i.e., finishing the treatment, the handle 8 is brought away from the stopper 9, releasing the treatment target from between the pair of grasps 18A and 18B.

When the angular position of the operating member 70 of the bending mechanism 6B with respect to the rotational axis C0 changes from the position illustrated in FIG. 3A to the position illustrated in FIG. 3B with respect to the housing 5, the end effector 15 is in the first bent position in which it is bent with respect to the distal end of the sheath 3. At this time, the engaging portions 55A and 55B engage in the groove 51 in the second engaging state described hereinbefore in which the engaging portion 55A engages in the groove 51 at the angular position 62a, or the second angular position, and the engaging portion 55B engages in the groove 51 at the angular position ε2b, or the second angular position.

At this time, due to the rotation of the main rotational shaft 62 caused by the operating member 70, the second slider 66 is retracted from the state illustrated in FIG. 3A to the state illustrated in FIG. 3B with respect to the tubular member 36 of the opening and closing mechanism 6A and the support body 61. Consequently, the first link 17A supported on the second slider 66 is pulled toward the proximal-end side along the longitudinal axis C. Since the first link 17A of the bending mechanism 6B is supported on the end effector 15 by the second link 17B, the end effector 15 is bent from the position illustrated in FIG. 3A to the position illustrated in FIG. 3B about the turning shafts 16 in ganged relation to the angular movement of the operating member 70. Therefore, the operating member 70 actuates the second drive shaft 17 so as to be movable between the bending position for bending the end effector 15 with respect to the sheath 3 and the neutral position in which the end effector 15 extends along the longitudinal axis C of the sheath 3. At this time, the first link 19A of the opening and closing mechanism 6A is kept parallel to the longitudinal axis C. As the end effector 15 is bent with respect to the distal end of the sheath 3, the second link 19B becomes offset from the state along the longitudinal axis C.

Figure 5B:
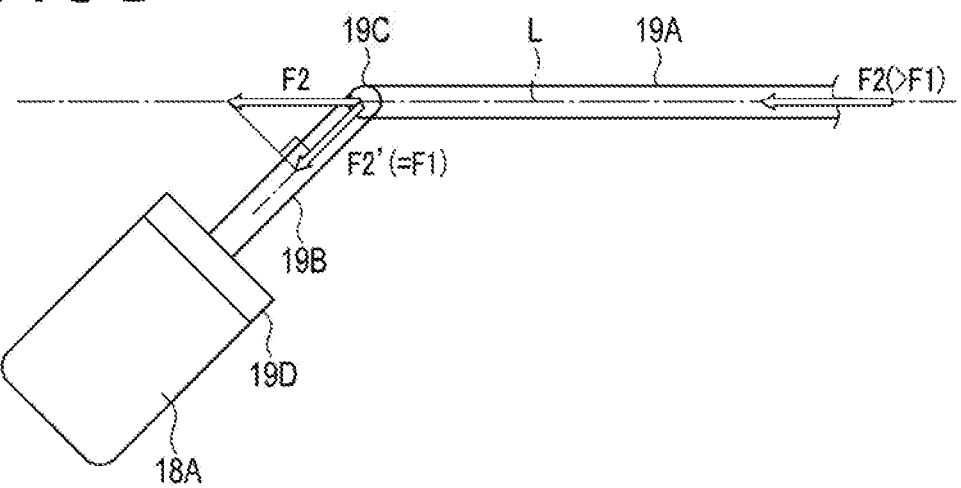
FIG. 5B is a schematic view illustrating an axial force transmitted to the first drive shaft disposed in the housing and the sheath at the time the opening and closing mechanism of the actuating mechanism is operated while the end effector of the treatment tool of the treatment system according to the first embodiment is in the bent position.

The handle 8 of the opening and closing mechanism 6A is closed with respect to the grip 5b and moved until it abuts against the stopper 9. As illustrated in FIG. 5B, the axial force F is transmitted successively to the first link 19A and the second link 19B in the order named, pushing the joint shaft 19D, i.e., the first grasp 18A, along the central axis of the base body 15A toward the distal-end side thereby to grip the treatment target between the grasps 18A and 18B.

As described hereinbefore, the adjusting mechanism 80 adjusts the movable range of the slider 37 with respect to the first drive shaft 19 while the handle 8 is abutting against the stopper 9. Therefore, the distance that the resilient member 38 is compressed while the handle 8 is abutting against the stopper 9 is larger in the second engaging state than in the first engaging state. Thus, the resilient force transmitted from the resilient member 38 to the first drive shaft 19 is larger in the second engaging state than in the first engaging state. Consequently, the axial force F transmitted to the first link 19A is larger in the second engaging state than in the first engaging state. In other words, an axial force F2 applied to the first link 19A of the first drive shaft 19 in the second engaging state is larger than the axial force F1 in the first engaging state.

In the first engaging state, inasmuch as the longitudinal axis of the first link 19A and the longitudinal axis of the second link 19B are coaxial with each other, transmission loss of the axial force from the first link 19A to the second link 19B is small. In the second engaging state, the longitudinal axis of the first link 19A and the longitudinal axis of the second link 19B are out of alignment with each other. Therefore, when an axial force is transmitted from the first link 19A to the second link 19B, a component F2' (<F2) of the axial force F2 transmitted to the first link 19A is transmitted to the second link 19B. A maximum gripping force that is exerted between the pair of grasps 18A and 18B at this time is referred to as a second gripping force.

Here, it is assumed that adjustments have been made to equalize the component F2' with the axial force F1 in the first engaging state, for example. At this time, the second gripping force exerted between the pair of grasps 18A and 18B while the end effector 15 is being bent with respect to the distal end of the sheath 3 can be substantially the same as the first gripping force exerted between the pair of grasps 18A and 18B while the end effector 15 is extending straight with respect to the distal end of the sheath 3.

When the surgeon enters an operation input through the operating device 13 while the treatment target is being gripped, the power supply device 10 supplies electric energy to the treatment tool 2. As described hereinbefore, treatment energy is applied to the treatment target, treating the gripped treatment target.

After applying the treatment energy to the gripped treatment target, i.e., finishing the treatment, the handle 8 is brought away from the stop 9, releasing the treatment target from between the pair of grasps 18A and 18B.

In the range from the angular position ε1a, or the first angular position, to the angular position, or the second angular position, around the longitudinal axis C, the width B of the groove 51 decreases continuously. In the range from the angular position ε1b, or the first angular position, to the angular position ε2b, or the second angular position, around the longitudinal axis C, the width B of the groove 51 decreases continuously. Therefore, providing other conditions are the same, the closer the position in which the engaging portion 55A engages in the groove 51 is to the angular position ε2a, or the second angular position, i.e., the closer the position in which the engaging portion 55B engages in the groove 51 is to the angular position ε2b, or the second angular position, the larger the axial force F transmitted from the resilient member 38 to the first drive shaft 19 becomes.

Similarly, when the operating member 70 of the bending mechanism 6B in the position illustrated in FIG. A is turned to the position illustrated in FIG. 3C, the end effector 15 moves from the neutral position to the second bent position. At this time, the second gear 64 held in mesh with the gear 70a of the operating member 70 rotates, causing the main rotational shaft 62 to rotate about the longitudinal axis C in ganged relation thereto. The rotation of the main rotational shaft 62 causes the circumferential gear 46b held in mesh with the gear assembly 84, or the rotary gear 71 in the support body 61, to rotate around the longitudinal axis C, rotating the second member 46 of the rotor assembly 40 around the longitudinal axis C. At this time, the second member 46 rotates in a direction opposite to the direction in which it rotates from the position illustrated in FIG. 4A to the position illustrated in FIG. 4B. The second member 46 is of a symmetrical shape with respect to the longitudinal axis C. Therefore, the engaging state in which the engaging portions 55A and 55B engage in the groove 51 changes successively from the first engaging state (see FIG. 4A) to the third engaging state.

In the third engaging state, consequently, as with the second engaging state, the axial force F transmitted to the first link 19A is larger than in the first engaging state. In other words, the axial force F applied to the first link 19A of the first drive shaft 19 in the third engaging state is larger than the axial force F1 in the first engaging state. Accordingly, a third gripping force exerted between the pair of grasps 18A and 18B while the end effector 15 is being bent to the second bent position with respect to the distal end of the sheath 3 can be substantially the same as the first gripping force exerted between the pair of grasps 18A and 18B while the end effector 15 is extending straight with respect to the distal end of the sheath 3.

The treatment tool 2 according to the present embodiment makes it possible to associate the circumferential position of the groove 51 in which the engaging portions 55A and 55B engage, with the angular position of the operating member 70. The treatment tool 2 is also able to set the width of the groove 51 along the longitudinal axis C to an appropriate value, for example, along circumferential directions. Therefore, regardless of whether the end effector 15 is in either the neutral position or the bent positions with respect to the distal end of the sheath 3, the axial force F transmitted to the first link 19A of the opening and closing mechanism 6A at the time the handle 8 is brought into abutment against the stopper 9 of the grip 5*b* can be set to an appropriate value. In the present embodiment, by way of example, the axial force, or an actuating force, of the first link 19A in a case where the end effector 15 is in the neutral position with respect to the distal end of the sheath 3 is made smaller than the axial force, or the actuating force, of the first link 19A in a case where the end effector 15 is in the bent positions. Therefore, the gripping force applied to grip the treatment target between the grasps 18A and 18B can be adjusted between the neutral position and the bent positions by adjusting the actuating force in the case where the end effector 15 is in the neutral position with respect to the distal end of the sheath 3 and the actuating force in the case where the end effector 15 is in the bent positions, i.e., the first bent position and the second bent position, with respect to the distal end of the sheath 3.

For example, the gripping force applied to grip the treatment target between the grasps 18A and 18B can be uniformized between the neutral position and the bent positions by configuring the groove 51 in an appropriate shape at the positions where the engaging portions 55A and 55B engage in the groove 51. Alternatively, it is possible to make the gripping force applied to grip the treatment target between the grasps 18A and 18B larger in the bent positions than in the neutral position by configuring the shape of the groove 51 in an appropriate shape. It is also possible to make the gripping force smaller in the bent positions than in the neutral position by setting the shape of the groove 51 with respect to the engaging portions 55A and 55B to an appropriate shape.

In the present embodiment, therefore, there is provided a treatment tool 2, or a medical instrument, capable of adjusting the axial force F that is transmitted to the drive shaft 19 for opening and closing the pair of grasps 18A and 18B relatively to each other in the case where the end effector 15 is in the neutral position with respect to the sheath 3 and in the case where the end effector 15 is in the bent positions with respect to the sheath 3. Particularly, the bent positions are not limited to the maximally bent positions (see FIGS. 3B and 3C) to which the end effector 15 is bent from the neutral position. Consequently, even when the end effector 15 is bent to any positions off the neutral position with respect to the sheath 3, the treatment tool 2, or the medical instrument, is capable of adjusting the axial force F that is transmitted to the first drive shaft 19 for opening and closing the pair of grasps 18A and 18B relatively to each other.

Figure 6:
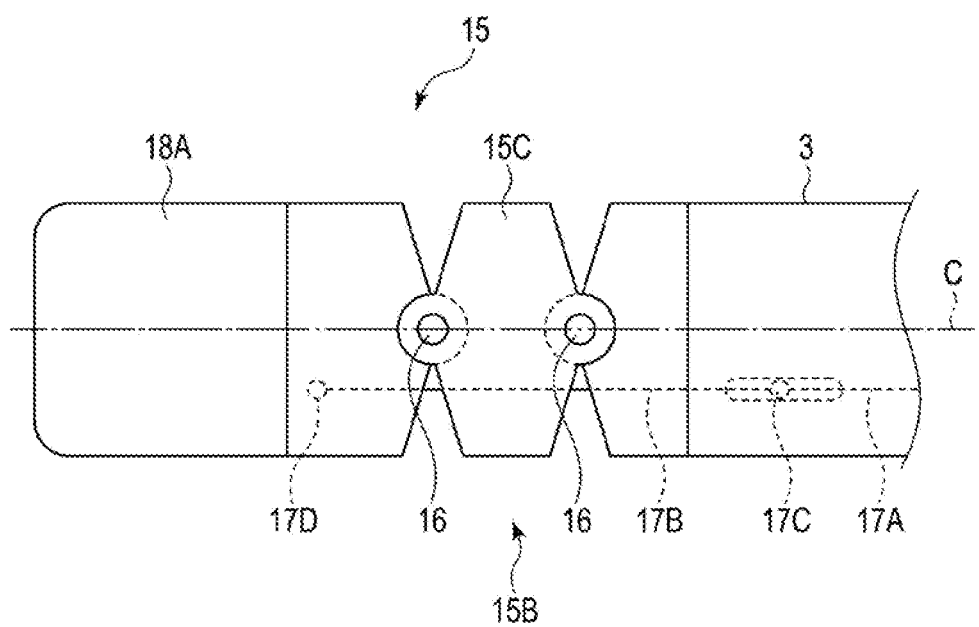
FIG. 6 is a schematic view illustrating a modification of the end effector of the treatment tool of the treatment system according to the first embodiment.

There are available various mechanisms for bending the base body 15A of the end effector 15 with respect to the longitudinal axis C of the sheath 3. Though those mechanisms will not be described in detail hereinafter as they are known in the art, it is preferable to use, instead of the base body 15A, a bendable tube 15B, or a direction changer, illustrated in FIG. 6 that includes a plurality of rings 15C coupled together by turning shafts 16. The bendable tube 15B is used in the bendable portion of an endoscope, for example. A bending mechanism for bending the end effector 15 with an appropriate radius of curvature with respect to the distal end of the sheath 3 may thus be used as a mechanism between the distal end of the sheath 3 and the grasps 18A and 18B of the end effector 15.

The second link 17B described hereinbefore may suitably be replaced with a wire, for example, instead of the rod, depending on the specifications of the bendable tube 15B.

First Modification

In the first embodiment described hereinbefore, the actuating mechanism 6 includes the opening and closing mechanism 6A and the bending mechanism 6B that are operatively linked with each other. Meanwhile, in the examples illustrated in FIGS. 3A through 4B, even when the knob 11 of the rotating mechanism 6C of the actuating mechanism 6 is rotated about the central axis C with respect to the housing 5, the operating member 70 of the bending mechanism 6B is not rotated about the central axis C with respect to the housing 5. Therefore, in the first embodiment described hereinbefore, the bending mechanism 6B and the rotating mechanism 6C of the actuating mechanism 6 are not operatively linked with each other. In the first modification, an example in which the opening and closing mechanism 6A and the bending mechanism 6B are operatively linked with each other and the bending mechanism 6B and the rotating mechanism 6C are operatively linked with each other will hereinafter be described.

Figure 7:
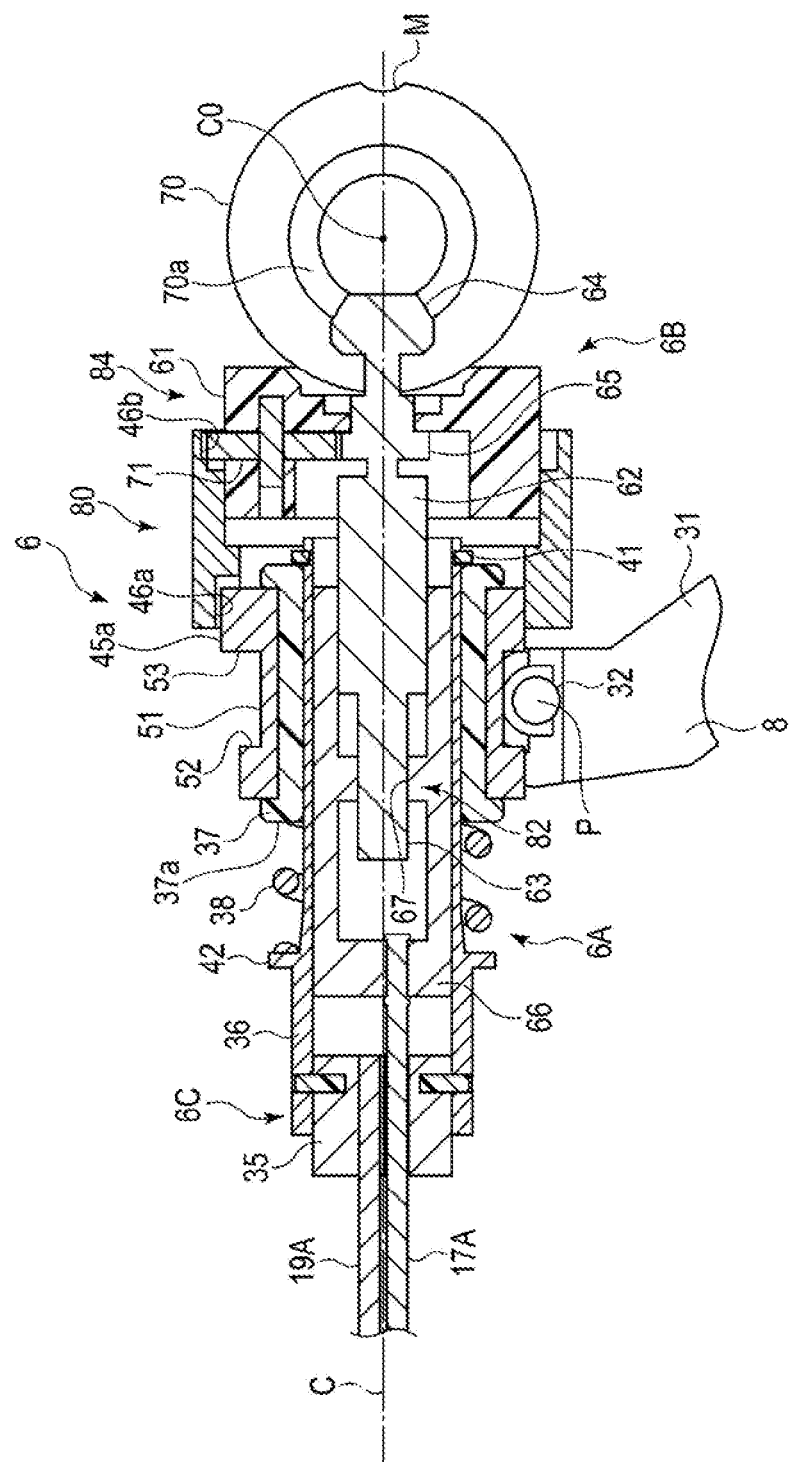
FIG. 7 is a schematic view illustrating a cross section of an actuating mechanism disposed in a housing of a treatment tool of a treatment system according to a first modification of the first embodiment.

The proximal-end portion of the first link 17A of the bending mechanism 6B described in the first embodiment is coupled to the second slider 66 on the longitudinal axis C, as illustrated in FIGS. 3A through 3C. In the first modification, as illustrated in FIG. 7, the proximal-end portion of the first link 17A of the bending mechanism 6B is coupled to the second slider 66 at a position parallel to and offset from the longitudinal axis C. In this case, the proximal-end portion of the first link 17A should also preferably be rotatable with respect to the second slider 66 by a bearing, for example.

In this case, when the rotary knob 11 of the rotating mechanism 6C is rotated about the longitudinal axis C, the first link 19A of the first drive shaft 19, the relay member 35, and the tubular member 36 are rotated in unison with the sheath 3 about the longitudinal axis C. Therefore, the end effector 15 is also rotated in unison with the sheath 3 about the longitudinal axis C. At this time, the first link 17A, the second slider 66, the support body 61, and the operating member 70 are rotated in unison with the tubular member 36.

Second Modification

Figure 8:
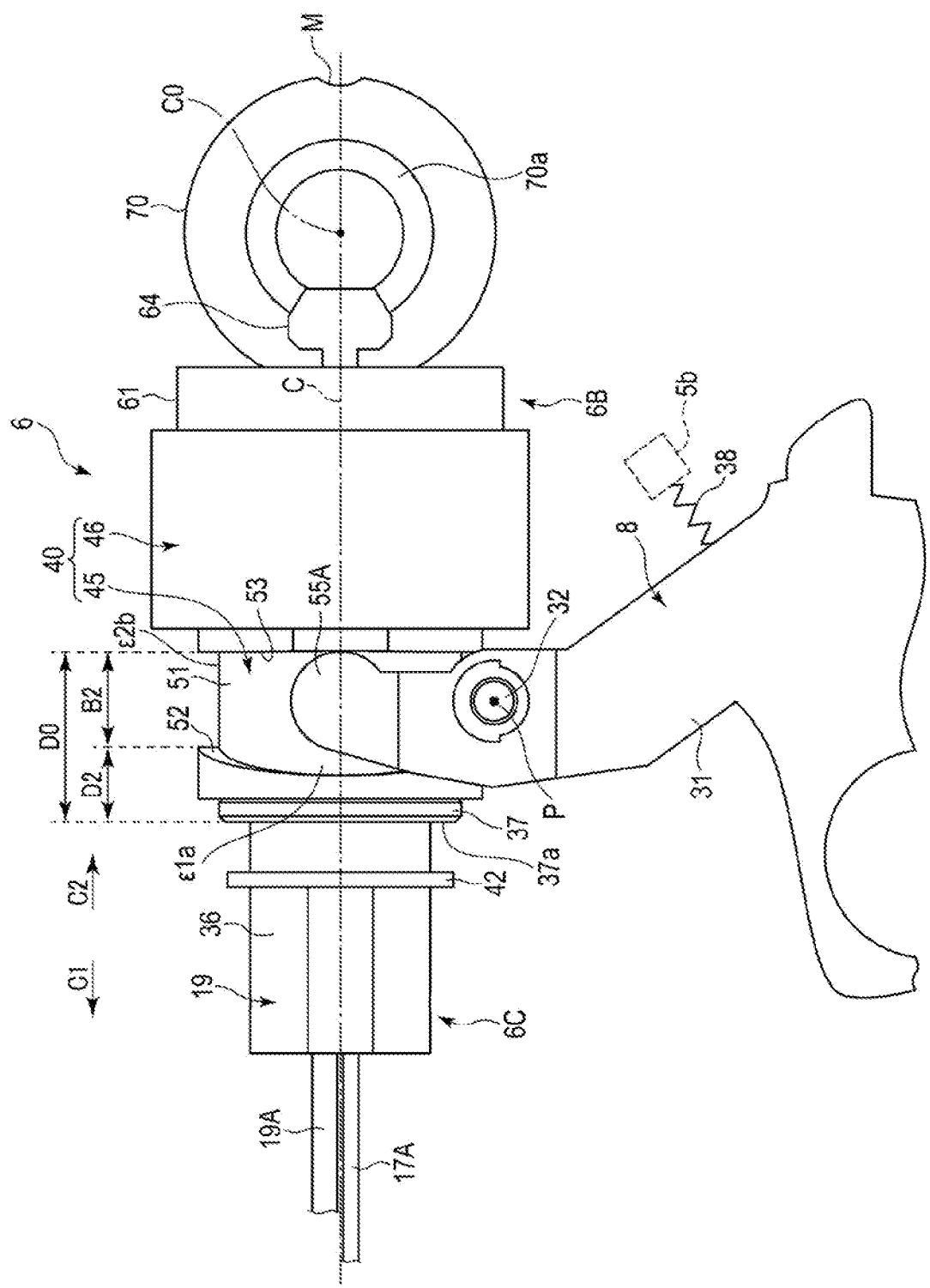
FIG. 8 is a schematic view illustrating an actuating mechanism disposed in a housing in a case where an end effector of a treatment tool of a treatment system according to a second modification of the first embodiment is in a neutral position.

In the first embodiment described hereinbefore, the resilient member 38 is disposed outside of and concentrically with the tubular member 36. As illustrated in FIG. 8, the resilient member 38 is not necessarily required to be disposed outside of and concentrically with the tubular member 36.

As illustrated in FIG. 8, the resilient member 38 may be disposed between the handle 8 and the grip 5*b*, instead of being disposed outside of the tubular member 36 or as well as being disposed outside of the tubular member 36. The resilient member 38 that is disposed between the handle 8 and the grip 5*b* may be a suitable resilient member such as a helical spring, a leaf spring, or the like.

Third Modification

Figure 9A:
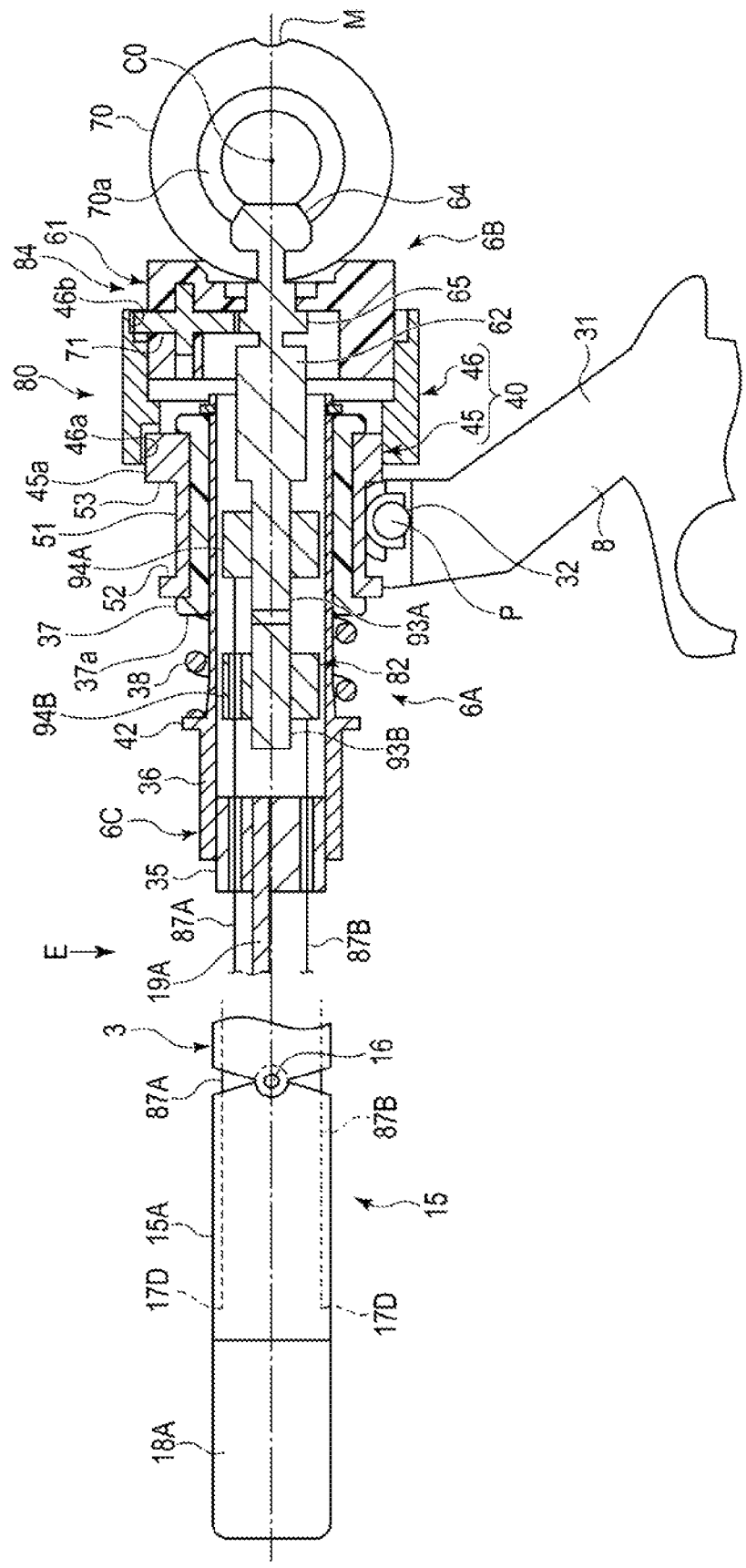
FIG. 9A is a schematic view illustrating a cross section of an actuating mechanism disposed in a housing of a treatment tool of a treatment system according to a third modification of the first embodiment and also illustrating a state, or a neutral position, of an end effector with respect to the actuating mechanism, as viewed from a direction of an arrow E in an area illustrated in cross section.

The bending mechanism 6B in the examples illustrated in FIGS. 3A through 4B uses the first link 17A, or the rod, and the second link 17B, or the rod, as the second drive shaft 17 for moving the end effector 15 between the neutral position and the bent positions with respect to the distal end of the sheath 3. As illustrated in FIG. 9A, the bending mechanism 6B in a third modification uses a pair of wires 87A and 87B, instead of the first link 17A and the second link 17B, as the second drive shaft 17. In this case, the support shaft 17C can be dispensed with. The distal end 17D of the second drive shaft 17, i.e., the distal ends of the wires 87A and 87B, is coupled to the base body 15A of the end effector 15.

Figure 9B:
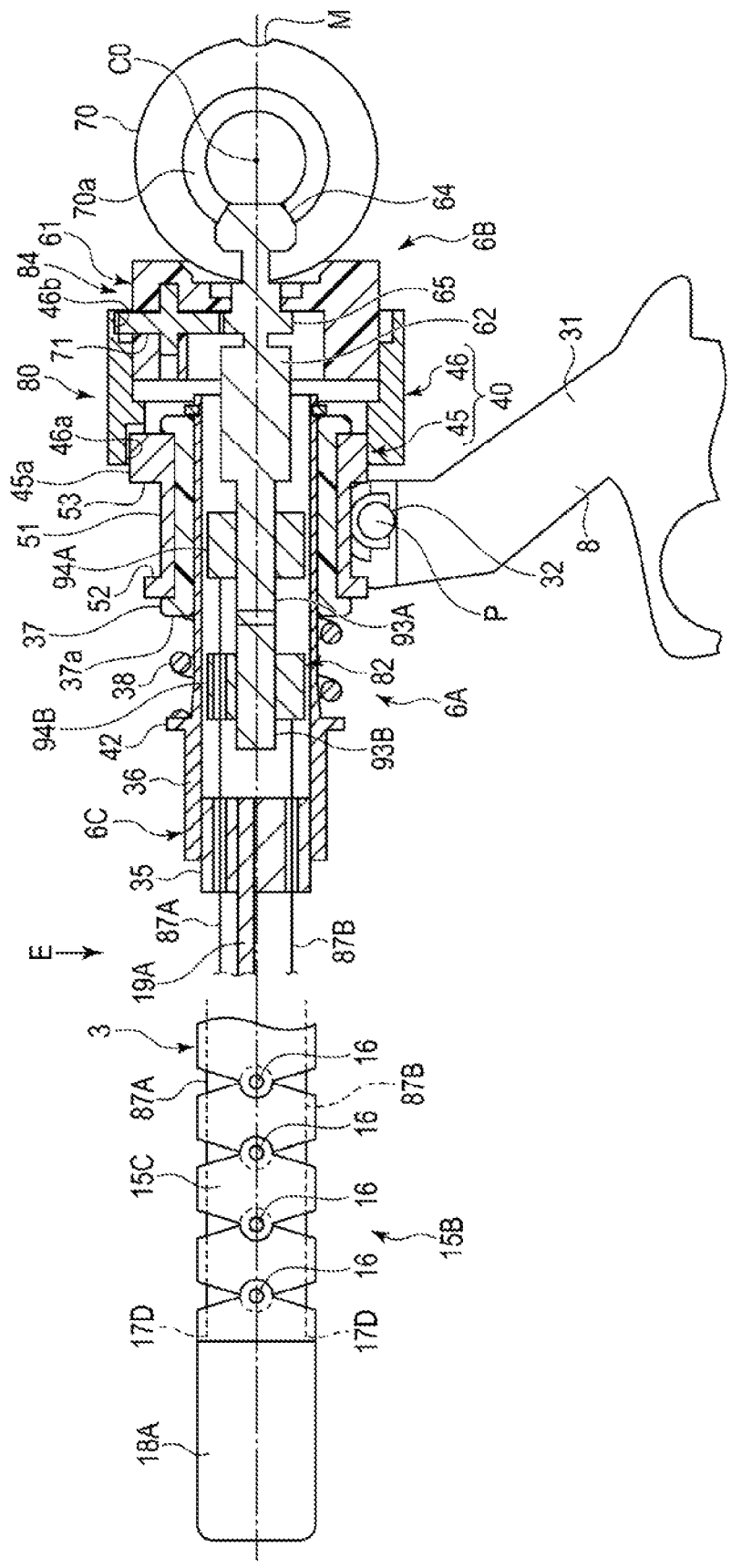
FIG. 9B is a schematic view illustrating a cross section of an actuating mechanism disposed in a housing of a treatment tool of a treatment system according to a further modification of the third modification of the first embodiment and also illustrating a state, or a neutral position, of an end effector with respect to the actuating mechanism, as viewed from a direction of an arrow E in an area illustrated in cross section.

The main rotational shaft 62 has a first externally threaded portion 93A and a second externally threaded portion 93B. The first externally threaded portion 93A and the second externally threaded portion 93B are threaded in opposite directions. Nuts 94A and 94B, or second sliders, are threaded respectively over the first externally threaded portion 93A and the second externally threaded portion 93B. The second gear 64, the first externally threaded portion 93A and the second externally threaded portion 93B of the main rotational shaft 62, and the nuts 94A and 94B function as a gear assembly 82 that moves the nuts 94A and 94B along the longitudinal axis C upon rotation of the operating member 70 and the main rotational shaft 62. The wire 87A has a proximal end fixed to the nut 94A, and the wire 87B has a proximal end fixed to the nut 94B. In FIGS. 9A and 9B, the wire 87A is illustrated as extending through the nut 94B. However, the wire 87A may be disposed outside of the nut 94B.

By way of example, when the operating member 70 is rotated about the rotational axis C0, the main rotational shaft 62 is rotated in a first direction about the longitudinal axis C. The first nut 94A moves forwardly along the longitudinal axis C as the main rotational shaft 62 rotates. The second nut 94B moves rearwardly along the longitudinal axis C as the main rotational shaft 62 rotates in the first direction. Therefore, the first nut 94A and the second nut 94B move relatively closer to each other. At this time, the first wire 87A connected to the first nut 94A moves forwardly, and the second wire 87B connected to the second nut 94B is pulled. Therefore, the end effector 15 that is supported on the distal end of the second wire 87B connected to the second nut 94B is pulled. The end effector 15 that is supported on the distal end of the sheath 3 by the turning shafts 16 is bent.

Similarly, as the main rotational shaft 62 rotates in a second direction opposite the first direction, the first nut 94A is retracted along the longitudinal axis C. The second nut 94B moves forwardly along the longitudinal axis C as the main rotational shaft 62 rotates in the second direction. At this time, the first wire 87A connected to the first nut 94A is pulled, and the second wire 87B connected to the second nut 94B moves forwardly. Therefore, the end effector 15 that is supported on the distal end of the first wire 87A connected to the first nut 94A is pulled. The end effector 15 that is supported on the distal end of the sheath 3 by the turning shafts 16 is bent.

At this time, the first member 45 is rotated about the longitudinal axis C in ganged relation to an operation of the operating member 70. Therefore, the bending mechanism 6B may use the nuts 94A and 94B and the wires 87A and 87B instead of the second slider 66, the first link 17A, and the second link 17B.

As illustrated in FIG. 9B, a bendable tube 15B that includes a plurality of rings 15C coupled together may be used in place of the base body 15A illustrated in FIG. 9A.
Fourth Modification In the first embodiment that includes the modifications described hereinbefore, when the handle 8 is turned about the support pin 32 toward the stopper 9, the first drive shaft 19 is moved along the longitudinal axis C toward the distal-end side with respect to the housing 5 and the sheath 3, exerting a gripping force between the pair of grasps 18A and 18B.

Figure 10:
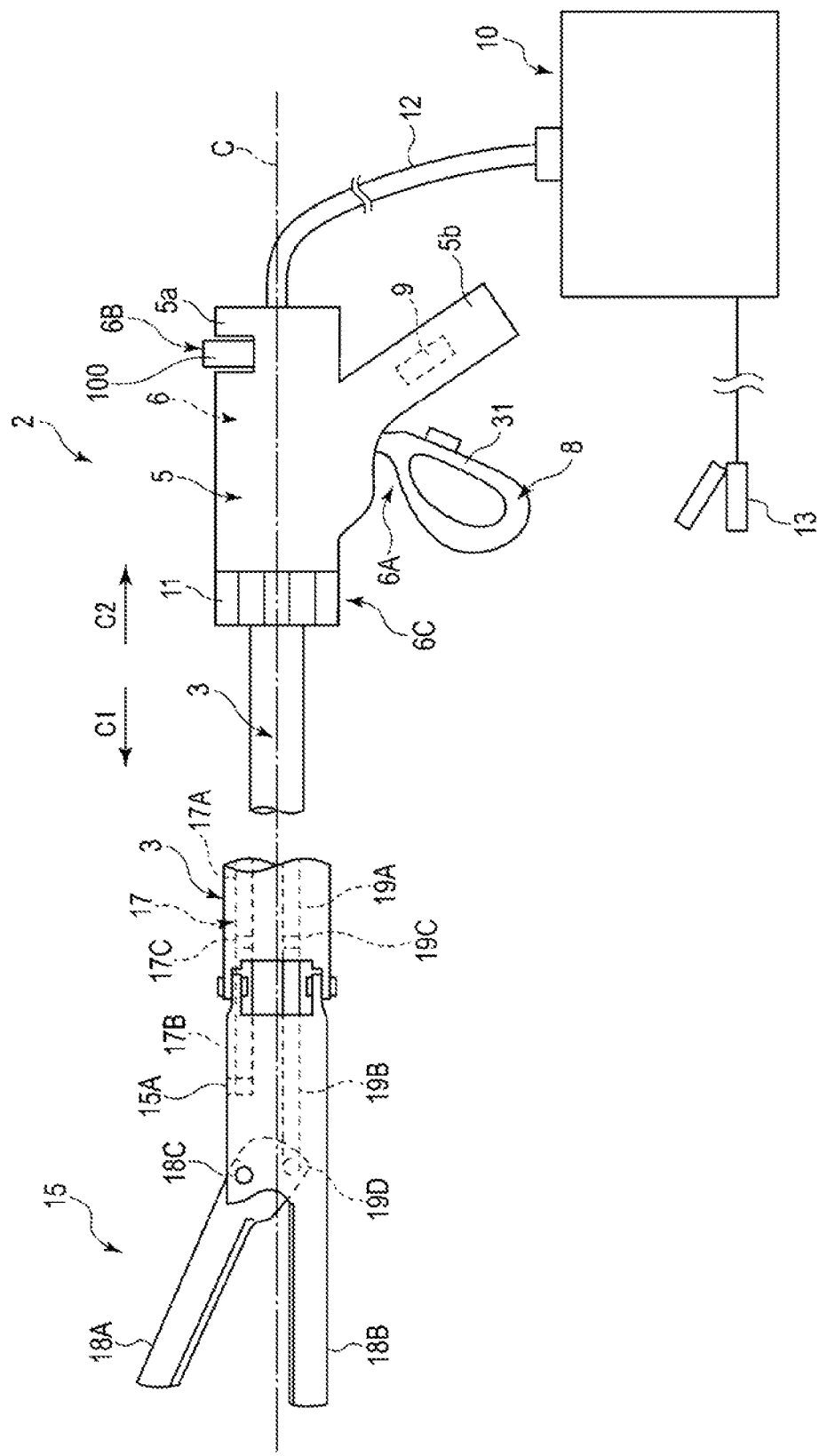
FIG. 10 is a schematic view illustrating a treatment system according to a fourth modification of the first embodiment and also illustrating at an enlarged scale an end effector of a treatment tool of the treatment system and parts in the vicinity of the end effector.
Figure 11:
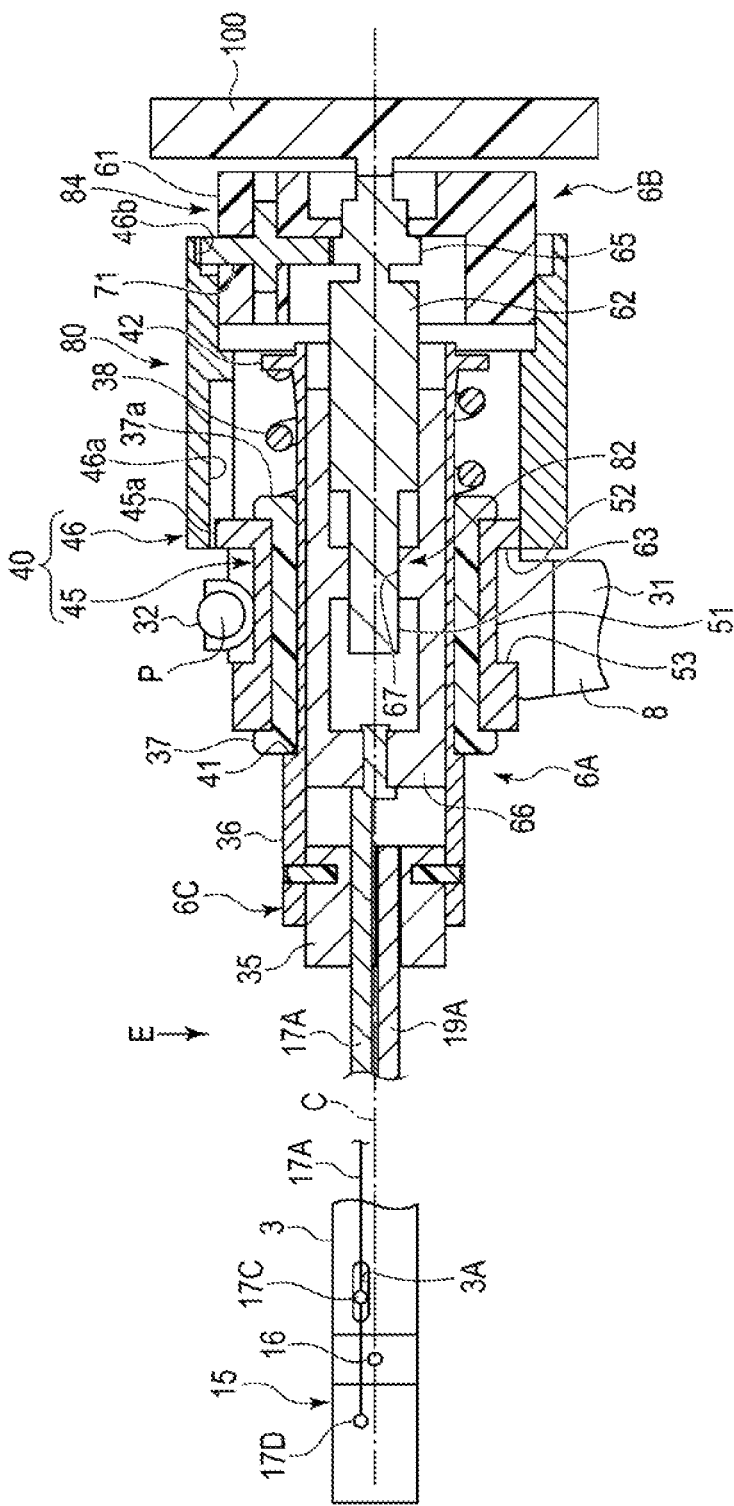
FIG. 11 is a schematic view illustrating a cross section of an actuating mechanism disposed in a housing of the treatment tool of the treatment system according to the fourth modification of the first embodiment and also illustrating a state, or a neutral position, of the end effector with respect to the actuating mechanism, as viewed from a direction of an arrow E in an area illustrated in cross section.
Figure 12:
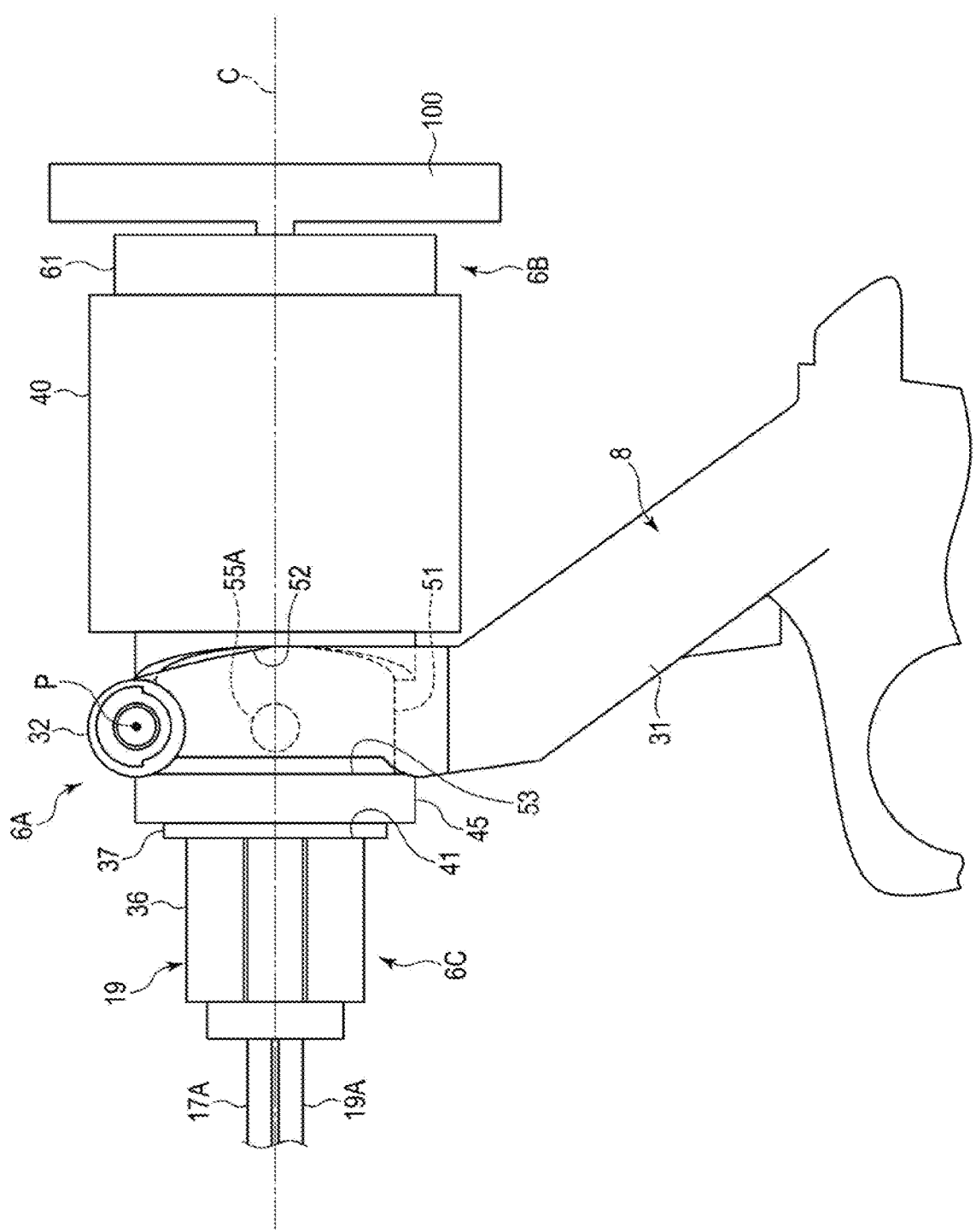
FIG. 12 is a schematic view illustrating the actuating mechanism disposed in the housing in a case where the end effector of the treatment tool of the treatment system according to the fourth modification of the first embodiment is in the neutral position.

In a fourth modification, as illustrated in FIGS. 10 through 12, when the first drive shaft 19 is moved along the longitudinal axis C toward the proximal-end side with respect to the housing 5 and the sheath 3, a gripping force is exerted between the pair of grasps 18A and 18B, as briefly described hereinafter.

In the housing 5, the handle 8 is angularly movably attached to the housing 5 by the support pin 32 illustrated in FIGS. 11 and 12. The support pin 32 has a central axis that functions as a turn axis P, or a turn center, about which the handle 8 is angularly movable. In the fourth modification, the tubular member 36 is disposed between the support pin 32, i.e., the turn axis P, and the protrusion 31 of the handle 8.

In the example illustrated in FIG. 3A according to the first embodiment, the ridge 42, the resilient member 38, and the slider 37 are successively disposed on the outer circumferential surface of the tubular member 36 in the order named from the distal-end side toward the proximal-end side. In the present modification, by way of example, the stopper 41, the slider 37, the resilient member 38, and the ridge 42 are successively disposed on the outer circumferential surface of the tubular member 36 in the order named from the distal-end side toward the proximal-end side.

The stopper 41 is disposed on the distal-end side of the slider 37 and fixed with respect to the first drive shaft 19. When the slider 37 abuts against the stopper 41, the slider 37 is restrained from moving into an area on the distal-end side of the stopper 41. In the present embodiment, furthermore, the ridge 42 that projects toward an outer circumferential side is disposed on the outer circumferential surface of the tubular member 36. The ridge 42 is, for example, integrally formed with the tubular member 36, and disposed on the proximal-end side of the slider 37.

The resilient member 38 is disposed on the outer circumferential surface of the tubular member 36 of the first drive shaft 19. The resilient member 38 extends along the longitudinal axis C between the ridge 42 and the slider 37. The resilient member 38 has an end, or a proximal end, held in contact with or connected to the ridge 42 of the first drive shaft 19. The resilient member 38 has another end, or a distal end, held in contact with or connected to the slider 37. Therefore, the resilient member 38 is disposed between the first drive shaft 19 and the slider 37 in the directions along the longitudinal axis C. As the slider 37 moves along the longitudinal axis C with respect to the first drive shaft 19, the resilient member 38 is expanded or compressed. Even when the slider 37 is in abutment against the stopper 41, i.e., when the slider 37 is most widely spaced from the ridge 42, the resilient member 38 is compressed from its natural length. Therefore, even when the slider 37 abuts against the stopper 41, a resilient force acts from the resilient member 38 on the first drive shaft 19 along the longitudinal axis C toward the proximal-end side. When the slider 37 is moved out of abutment against the stopper 41 toward the proximal-end side with respect to the first drive shaft 19, the resilient member 38 is further compressed, increasing the resilient force acting from the resilient member 38 on the first drive shaft 19.

In the first embodiment, the operating member 70 transmits forces through the gear 70*a* and the second gear 64 to the main rotational shaft 62. In the fourth modification, an operating member 100 is directly coupled to the proximal end of the main rotational shaft 62. The operating member 100 is rotatable about the longitudinal axis C. Therefore, the gear 70*a* and the second gear 64 described in the first embodiment are not necessarily required. The operating member 100 is of a substantially disk-shaped, though it may be in the form of a lever rotatable about the longitudinal axis C.

The first member 45 of the rotor assembly 40 is directed toward an opposite side to the first embodiment. In the present modification, the first groove side face 52 is directed toward the distal-end side. The second groove side face 53 is directed toward the proximal-end side.

When the handle 8 is most widely opened from the grip 5b, each of the engaging portions 55A and 55B abuts against the second groove side face 53 from the proximal-end side in the groove 51 and is spaced from the first groove side face 52 toward the distal-end side. Furthermore, when the handle 8 is most widely opened from the grip 5b, the slider 37 abuts against the stopper 41. For gripping a treatment target between the grasps 18A and 18B, the treatment target is placed between the grasps 18A, 18B while the handle 8 is being most widely opened from the grip 5b, and then the handle 8 is closed toward the grip 5b. Each of the engaging portions 55A and 55B in the groove 51 is now moved about the support pin 32 toward the first groove side face 52 in a direction toward the proximal-end side, and is brought into abutment against the first groove side face 52 from the distal-end side.

As each of the engaging portions 55A and 55B abuts against the first groove side face 52, each of the engaging portions 55A and 55B presses the first groove side face 52 toward the proximal-end side, transmitting the pressing force through the first member 45 of the rotor assembly 40, the slider 37, and the resilient member 38 to the first drive shaft 19. The first drive shaft 19 is thus moved together with the first member 45, the slider 37, and the resilient member 38 toward the proximal-end side with respect to the housing 5 and the sheath 3. As the first drive shaft 19 is moved toward the proximal-end side, the joint shaft 19D on the distal end of the first drive shaft 19 is moved toward the proximal-end side, whereupon at least one of the grasps 18A and 18B is moved angularly with respect to the base body 15A, closing the grasps 18A and 18B relatively to each other. At this time, the grasp 18A and/or the grasp 18B is moved angularly until the treatment target therebetween is compressed to a certain extent, and the grasps 18A and 18B are closed relatively to each other until the treatment target therebetween is compressed to a certain extent.

When the gripped treatment target is compressed to a certain extent, the grasp 18A and/or the grasp 18B stops being moved angularly, and the first drive shaft 19 also stops being moved toward the proximal-end side with respect to the housing 5 and the sheath 3.

Then, when the handle 8 is closed with respect to the grip 5b until the handle 8 abuts against the stopper 9, the pressing force from each of the engaging portions 55A and 55B is transmitted through the first member 45 to the slider 37, which is moved toward the proximal-end side with respect to the first drive shaft 19. The resilient member 38 is thus compressed, increasing the resilient force that acts from the resilient member 38 on the first drive shaft 19 toward the proximal-end side. As the resilient force from the resilient member 38 to the first drive shaft 19 is increased, the griping force applied to the treatment target between the grasps 18A and 18B is increased.

As the operating member 100 is rotated in the same manner as when the operating member 70 is rotated as described according to the first embodiment, the first member 45 is rotated. Consequently, when the handle 8 is closed with respect to the grip 5b until the handle 8 abuts against the stopper 9, the axial force F transmitted to the first link 19A of the opening and closing mechanism 6A is adjusted depending on the relationship between the width B of the groove 51 in the first member 45 and the engaging portions 55A and 55B. Therefore, the gripping force between the grasps 18A and 18B is appropriately adjusted when the end effector 15 is between the neutral position and the bent positions, i.e., the first bent position and the second bent position, with respect to the distal end of the sheath 3.

Other structural and operational details are the same as those described in the first embodiment, and their description will be omitted.

In the present modification, therefore, there is provided a treatment tool 2, or a medical instrument, capable of adjusting the axial force F that is transmitted to the first drive shaft 19 for opening and closing the pair of grasps 18A and 18B relatively to each other in a case where the end effector 15 is in the neutral position with respect to the sheath 3 and in a case where the end effector 15 is in the bent positions with respect to the sheath 3. The bent positions are not limited to the maximally bent positions to which the end effector 15 is bent from the neutral position. Consequently, even when the end effector 15 is bent to any positions off the neutral position with respect to the sheath 3, the treatment tool 2, or the medical instrument, is capable of adjusting the axial force F that is transmitted to the first drive shaft 19 for opening and closing the pair of grasps 18A and 18B relatively to each other.

Second Embodiment

Next, a second embodiment will hereinafter be described with reference to FIGS. 13A and 13B. The second embodiment represents a modification of the first embodiment including various modifications. Those parts which are identical to or those parts which have identical functions to those described according to the first embodiment are denoted by as identical numeral reference as possible, and will not hereinafter be described in detail.

In the first embodiment, the width along the longitudinal axis C of the groove 51 in the first member 45 of the rotor assembly 40 varies at positions that are 90° spaced apart circumferentially around the longitudinal axis C, for example. In the present embodiment, the rotor assembly 40 may be dispensed with. Therefore, in the present embodiment, the slider 37 has a groove 151 that is different from the groove 51 described hereinbefore. The groove 151 has a width along the longitudinal axis C that is uniform or substantially uniform at any position.

The actuating mechanism 6 is unitized and supported in the housing 5. The opening and closing mechanism 6A and the bending mechanism 6B are operatively linked with each other through the housing 5. The actuating mechanism 6 and the housing 5 can be moved relatively to each other along the longitudinal axis C of the sheath 3.

For the sake of brevity, the treatment tool 2 will be described as lacking the rotating mechanism 6C rotating the actuating mechanism 6 about the longitudinal axis C.

Figure 13B:
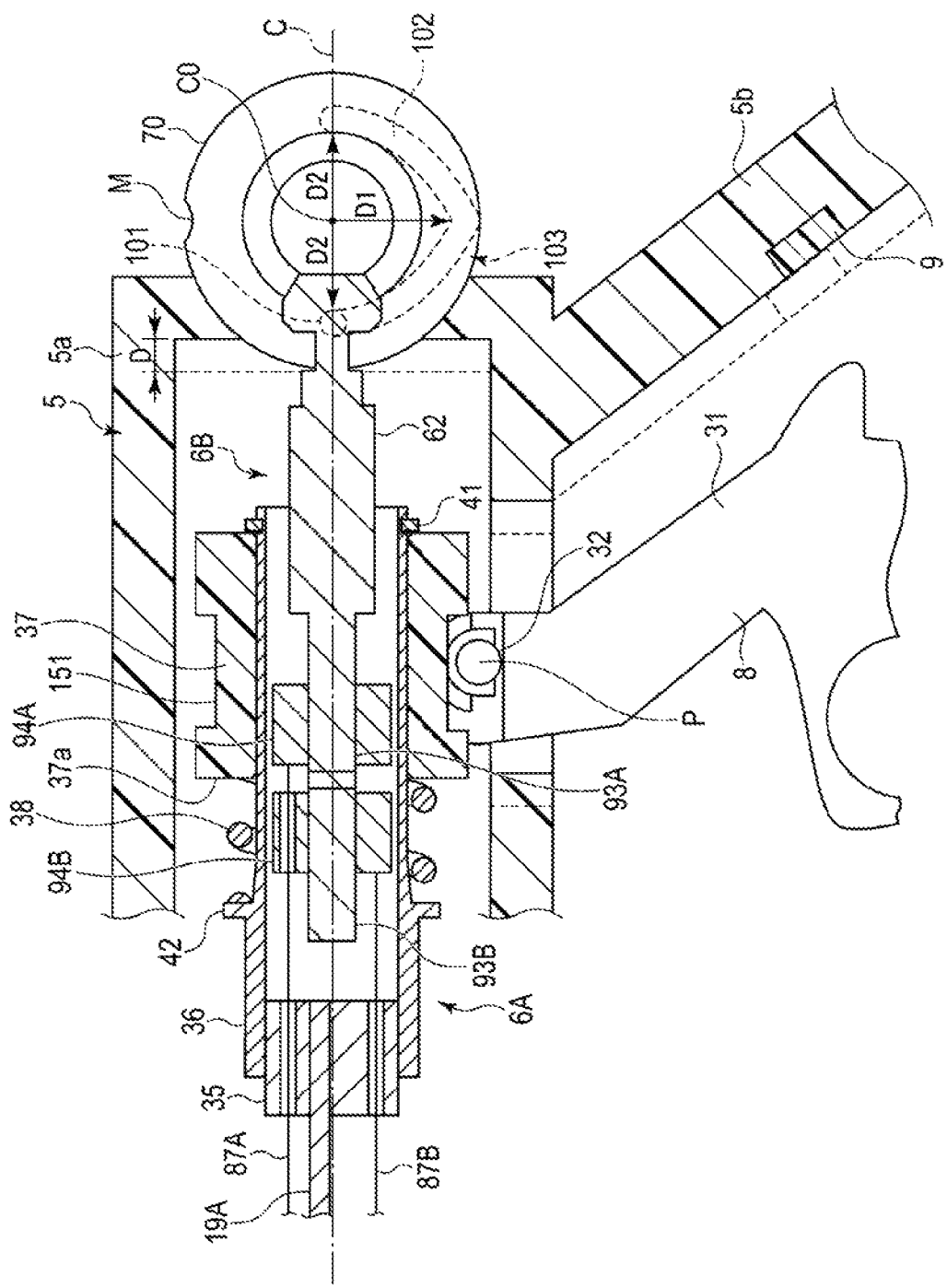
FIG. 13B is a schematic view illustrating a cross section of the actuating mechanism disposed in the housing in a case where the end effector of the treatment tool of the treatment system according to the second embodiment is in a bent position.

As illustrated in FIGS. 13A and 13B, the housing 5 has a pin 101, or a cam pin, as a first engaging portion projecting in a direction perpendicular to the longitudinal axis C. The operating member 70 of the bending mechanism 6B has a cam groove 102 as a second engaging portion in which the pin 101 engages. The operating member 70 has a circular outer profile. In the position illustrated in FIG. 13A, the cam groove 102 is in a position close to an outer circumferential surface of the operating member 70. In the position illustrated in FIG. 13B, the cam groove 102 is in a position closer to the rotational axis C0 than the position close to the outer circumferential surface of the operating member 70, i.e., in a position close to an outer circumferential surface of the gear 70a. In the case where the end effector 15 is in the neutral position with respect to the distal end of the sheath 3, the cam groove 102 is spaced a distance D1 from the rotational axis C0. In the case where the end effector 15 is in the bent positions with respect to the distal end of the sheath 3, the cam groove 102 is spaced a distance D2 (<D1) from the rotational axis C0. The distance D between the rotational axis C0 of the operating member 70 and the cam groove 102 is progressively smaller as the end effector 15 is bent from the neutral position toward the maximally bent positions of the bent positions. Therefore, the pin 101 and the cam groove 102 adjust the positional relationship between the housing 5 and the handle 8 depending on their engaging position.

When the operating member 70 is turned from the position illustrated in FIG. 13A to the position illustrated in FIG. 13B, for example, the position where the pin 101 engages in the cam groove 102 changes. Therefore, the housing 5 is moved along the longitudinal axis C toward the proximal-end side with respect to the actuating mechanism 6. Stated otherwise, the actuating mechanism 6 is moved along the longitudinal axis C toward the distal-end side with respect to the housing 5. For example, they are relatively moved by the distance D illustrated in FIG. 13B which is represented by D1-D2. Therefore, as the end effector 15 is bent toward the bent positions (see FIG. 13B) with respect to the distal end of the sheath 3, the distance between the handle 8 and the stopper 9 in the grip 5b becomes larger than when the end effector 15 is in the neutral position (see FIG. 13A) with respect to the distal end of the sheath 3. Consequently, the handle 8 has a larger movable range in the bent positions than in the neutral position. As the movable range increases, the distance that the slider 37 moves with respect to the first drive shaft 19, i.e., the distance that the resilient member 38 is compressed, increases. Therefore, when the handle 8 is brought into abutment against the stopper 9, the axial force F transmitted through the slider 37 to the first drive shaft 19 in the bent positions becomes larger than in the neutral position. The pin 101 and the cam groove 102 thus function as an adjusting mechanism 103 that adjusts the movable range of the slider 37 with respect to the first drive shaft 19 depending on the operated state of the operating member 70.

When the axial force is transmitted from the first link 19A to the second link 19B, a component F2' of the axial force F2 transmitted to the first link 19A along the longitudinal axis C is transmitted to the second link 19B in the bent positions, as illustrated in FIG. 5B. At this time, the axial force F2' adjusted with respect to the neutral position is transmitted to the first grasp 18A of the end effector 15. The gripping force between the grasps 18A and 18B is accordingly adjusted. Particularly, as the bent angle in the bent positions increases, the axial force F transmitted to the first drive shaft 19 is increased. By way of example, therefore, the treatment tool 2 according to the present embodiment is able to make the gripping force between the grasps 18A and 18B uniform or substantially uniform when the handle 8 is brought into abutment against the stopper 9 regardless of whether the end effector 15 is in the neutral position or the bent positions.

The example in which the actuating mechanism 6 is moved along the longitudinal axis C with respect to the housing 5 using the pin 101 and the cam groove 102 has been described hereinbefore. A similar structure may be realized using a gear on the housing 5 and a gear, different from the gear 70a, on the operating member 70, instead of the pin 101 and the cam groove 102.

The rotor assembly 40 and the support body 61 of the bending mechanism 6B described in the first embodiment may be disposed outside of the main rotational shaft 62 of the present embodiment. In this case, the actuating mechanism 6 itself is able to adjust the movable range of the handle 8 depending on the position of the end effector 15 with respect to the distal end of the sheath 3. In addition, the gripping force between the grasps 18A, 18B in the bent positions can be adjusted by moving the actuating mechanism 6 with respect to the housing 5. Therefore, the structure of the actuating mechanism 6 of the first embodiment and the structure of the actuating mechanism 6 of the second embodiment may be appropriately combined with each other.

First Modification

Figure 14A:
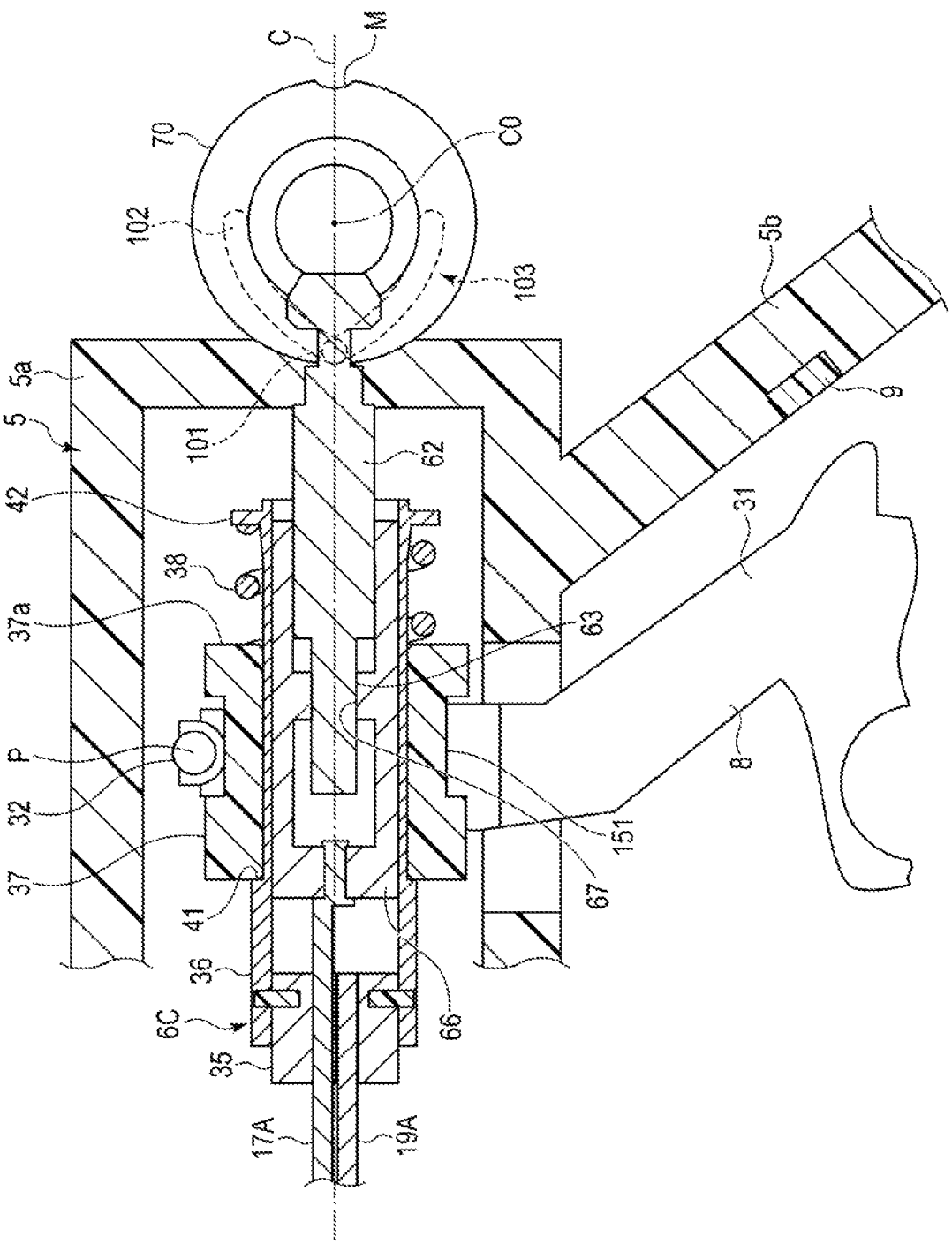
FIG. 14A is a schematic view illustrating a cross section of an actuating mechanism disposed in a housing in a case where an end effector of a treatment tool of a treatment system according to a first modification of the second embodiment is in a neutral position.
Figure 14B:
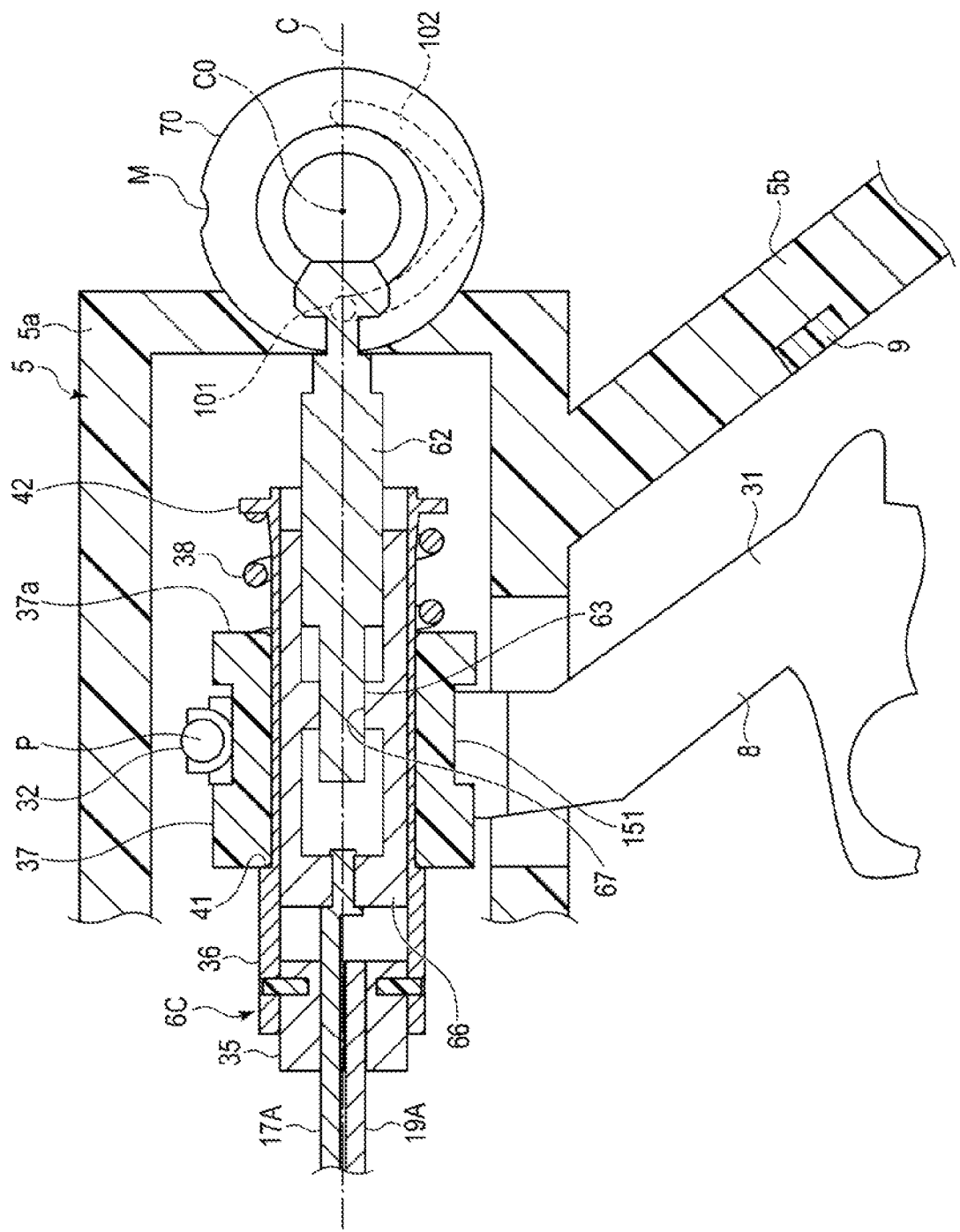
FIG. 14B is a schematic view illustrating a cross section of the actuating mechanism disposed in the housing in a case where the end effector of the treatment tool of the treatment system according to the first modification of the second embodiment is in a bent position.

FIGS. 14A and 14B illustrate the support pin 32 of the handle 8 that is disposed in the same position as the position illustrated in FIGS. 11 and 12 according to the first embodiment. As illustrated in FIGS. 14A and 14B, the adjusting mechanism 103, i.e., the pin 101 and the groove 102, may be disposed in the same manner as if the support pin 32 is disposed as illustrated in FIGS. 13A and 13B.

In the example illustrated in FIG. 14A, the end effector 15 is in the neutral position with respect to the distal end of the sheath 3. In this case, the movable handle 8 and the stopper 9 are positioned closest to each other. When the movable handle 8 is moved toward the stopper 9, the slider 37 and the tubular member 36 are moved along the longitudinal axis C toward the proximal-end side. Therefore, the slider 37 and the first link 19A and the second link 19B of the first drive shaft 19 are moved along the longitudinal axis C toward the proximal-end side. Therefore, the grasps 18A and 18B are closed relatively to each other. The handle 8 is further moved until it abuts against the stopper 9. As the handle 8 is moved, an axial force F is transmitted from the resilient member 38 through the tubular member 36 to the first link 19A. The maximum axial force F at this time is represented by F1.

In the example illustrated in FIG. 14B, the end effector 15 is in the bent positions with respect to the distal end of the sheath 3. In this case, the movable handle 8 and the stopper 9 are most widely spaced from each other. When the movable handle 8 is moved toward the stopper 9, the grasps 18A and 18B are closed relatively to each other, in the same manner as described hereinbefore. The handle 8 is further moved until it abuts against the stopper 9. As the handle 8 is moved, an axial force F is transmitted from the resilient member 38 through the tubular member 36 to the first link 19A. The maximum axial force F at this time is represented by F2. The movable handle 8 can be moved toward the stopper 9 by a larger distance in the state illustrated FIG. 14B than in the state illustrated in FIG. 14A. Consequently, the axial force F2 transmitted from the resilient member 38 through the tubular member 36 to the first link 19A is larger than the axial force F1 because of the action of the resilient member 38.

Therefore, regardless of whether the opening and closing mechanism 6A is of the structure illustrated in FIGS. 13A and 13B or the structure illustrated in FIGS. 14A and 14B, the gripping force between the grasps 18A, 18B is appropriately adjusted when the end effector 15 is in the neutral position and when the end effector 15 is in the bent positions, using the adjusting mechanism 103.

Second Modification

Figure 15A:
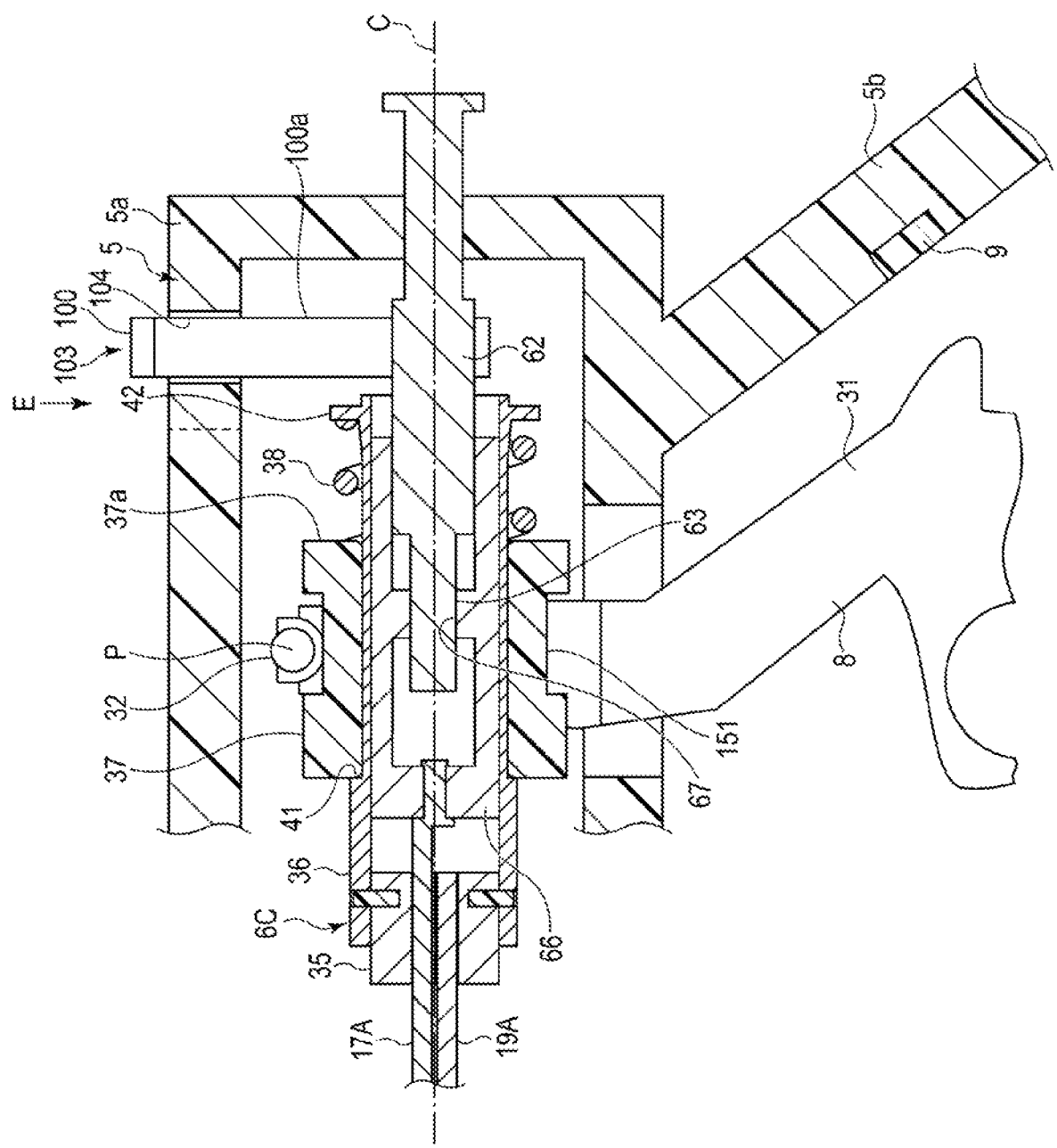
FIG. 15A is a schematic view illustrating a cross section of an actuating mechanism disposed in a housing in a case where an end effector of a treatment tool of a treatment system according to a second modification of the second embodiment is in a neutral position.
Figure 15B:
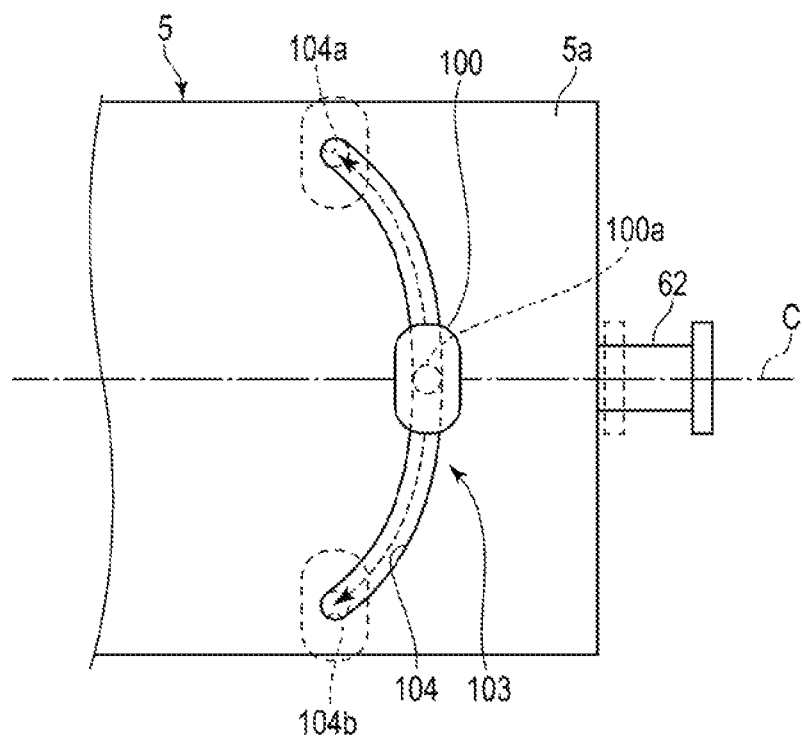
FIG. 15B is a schematic view illustrating the housing as viewed from a direction of an arrow E in FIG. 15A.

A second modification of the treatment tool 2 will hereinafter be described with reference to FIGS. 15A and 15B. FIG. 15A illustrates an example that uses an operating member 100 connected to the main rotational shaft 62, in place of the operating member 70. FIG. 15B illustrates a portion of the main housing body 5a of the housing 5 as viewed from a direction of an arrow E in FIG. 15A. The main housing body 5a of the housing 5 has a groove 104 that defines an angular movement range in which the operating member 100 is angularly movable about the longitudinal axis C. The groove 104 is of a substantially arcuate shape inclined to the longitudinal axis C. The groove 104 is directed toward the distal-end side along the longitudinal axis C in a direction from the center toward an end 104a. The groove 104 is directed toward the distal-end side along the longitudinal axis C in a direction from the center toward another end 104b. The operating member 100 has a rod 100a formed as a lever extending from the main rotational shaft 62 radially of the longitudinal axis C, for example.

In a case where the operating member 100 is positioned intermediate between the end 104a and the other end 104b of the groove 104, the end effector 15 is in the neutral position (see FIG. 3A). In a case where the operating member 100 is positioned in the end 104a of the groove 104, the end effector 15 is in the first bent position (see FIG. 3B), for example. In a case where the operating member 100 is positioned in the end 104b of the groove 104, the end effector 15 is in the second bent position (see FIG. 3C), for example.

When the operating member 100 is moved from the central position toward the end 104a, the actuating mechanism 6 is moved along the longitudinal axis C toward the distal-end side with respect to the housing 5. Similarly, when the operating member 100 is moved from the central position toward the other end 104b, the actuating mechanism 6 is moved along the longitudinal axis C toward the distal-end side with respect to the housing 5.

Therefore, as the end effector 15 is bent toward the bent positions with respect to the distal end of the sheath 3, the distance between the handle 8 and the stopper 9 in the grip 5b becomes larger than when the end effector 15 is in the neutral position with respect to the distal end of the sheath 3. Consequently, the handle 8 has a larger movable range in the bent positions than in the neutral position. As the movable range increases, the distance that the slider 37 moves with respect to the first drive shaft 19, i.e., the distance that the resilient member 38 is compressed, increases. Therefore, when the handle 8 is brought into abutment against the stopper 9, the axial force F transmitted through the slider 37 to the first drive shaft 19 in the bent positions becomes larger than in the neutral position. The groove 104 defined in the housing 5 and the rod 100a between the operating member 100 and the main rotational shaft 62 thus function as an adjusting mechanism 103 that adjusts the movable range of the slider 37 with respect to the first drive shaft 19 depending on the operated state of the operating member 100.

Third Modification

A third modification of the treatment tool 2 will hereinafter be described with reference to FIGS. 16A and 16B.

As described hereinbefore, the actuating mechanism 6 is unitized in the housing 5. The actuating mechanism 6 is supported with some backlash in the housing 5. Meanwhile, the housing 5 supports the support pin 32 of the actuating mechanism 6.

When an operation input is applied to the operating member 70, the end effector 15 is bent to a bent position offset from the neutral position in which the end effector 15 extends along the central axis C with respect to the distal end of the sheath 3.

The tubular member 36 has a pair of slits 36A and 36B defined in a distal-end side thereof. The slits 36A and 36B extend straight or substantially straight from the distal end of the tubular member 36 to the ridge 42. A first hook pin 95A is fixed to the first wire 87A. A second hook pin 95B is fixed to the second wire 87B. In the neutral position, the first hook pin 95A and the second hook pin 95B should preferably be directed in opposite directions to each other. The knob 11 has cavities 11A and 11B defined therein. The cavities 11A and 11B confront the longitudinal axis C. Each of the cavities 11A and 11B has an appropriate depth from an inner circumferential surface of the knob 11 and defines a movement range of the first hook pin 95A and the second hook pin 95B along the longitudinal axis C.

The first hook pin 95A extends through the slit 36A in the tubular member 36 and includes a remote portion that is remote from the longitudinal axis C and is disposed in the first cavity 11A. The second hook pin 95B extends through the slit 36B in the tubular member 36 and includes a remote portion that is remote from the longitudinal axis C and is disposed in the second cavity 11B.

In the neutral position, as illustrated in FIG. 16A, the first hook pin 95A is close to or is held in contact with a wall surface, closest to the proximal-end side, of the first cavity 11A, and the second hook pin 95B is close to or is held in contact with a wall surface, closest to the proximal-end side, of the second cavity 11B.

Figure 16B:
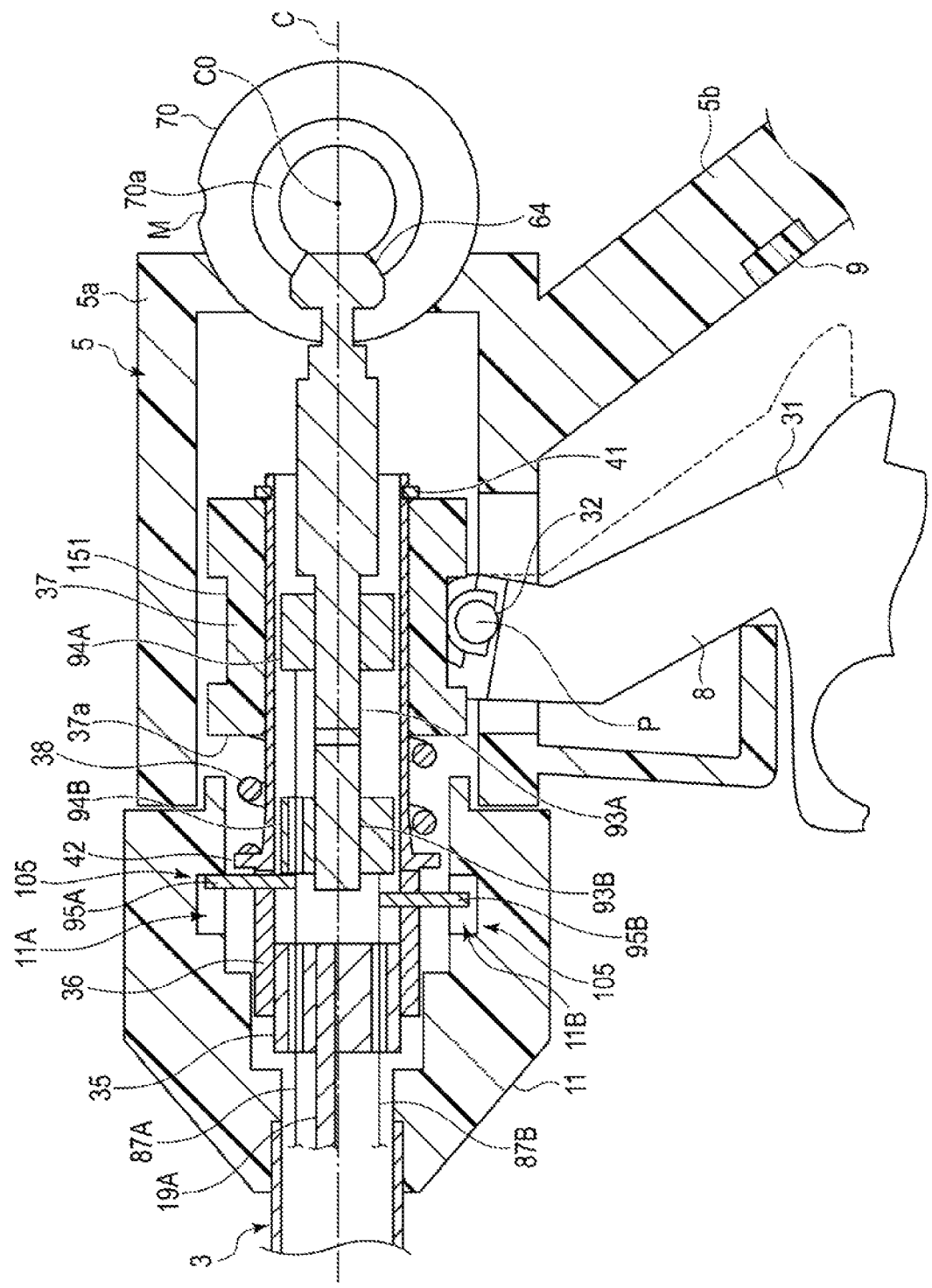
FIG. 16B is a schematic view illustrating a cross section of the actuating mechanism disposed in the housing in a case where the end effector of the treatment tool of the treatment system according to the third modification of the second embodiment is in a bent position.

In a case where the end effector 15 is bent from the neutral position to a bent position with respect to the distal end of the sheath 3, the operating member 70 is turned from the position illustrated in FIG. 16A to the position illustrated in FIG. 16B, rotating the main rotational shaft 62. For example, the first nut 94A is moved along the longitudinal axis C toward the proximal-end side, and the second nut 94B is moved along the longitudinal axis C toward the distal-end side.

When the first nut 94A is moved along the longitudinal axis C toward the proximal-end side, for example, the first wire 87A is moved along the longitudinal axis C toward the proximal-end side in ganged relation to the first nut 94A. Therefore, the end effector 15 is bent from the position illustrated in FIG. 3A to the position illustrated in FIG. 3B with respect to the distal end of the sheath 3. The first hook pin 95A fixed to the first wire 87A presses the wall surface, closest to the proximal-end side, of the first cavity 11A along the longitudinal axis C toward the proximal-end side. Therefore, the actuating mechanism 6 is moved in unison with the knob 11 along the longitudinal axis C toward the proximal-end side with respect to the housing 5. At this time, the central axes of the knob 11 and the sheath 3 and the central axis of the actuating mechanism 6 can be inclined to each other.

When the first nut 94A is moved along the longitudinal axis C toward the proximal-end side, for example, the second nut 94B is moved along the longitudinal axis C toward the distal-end side. Therefore, the second wire 87B is moved along the longitudinal axis C toward the distal-end side. Therefore, the second hook pin 95B fixed to the second wire 87B moves from the wall surface, closest to the proximal-end side, of the second cavity 11B along the longitudinal axis C toward the distal-end side. Accordingly, the remote portion of the second hook pin 95B is positioned between the wall surface, closest to the proximal-end side, of the second cavity 11B and the wall surface, closest to the distal-end side, thereof.

Since the housing 5 supports the support pin 32 of the actuating mechanism 6, the support pin 32 of the handle 8 is not moved with respect to the housing 5. Consequently, when the actuating mechanism 6 is moved along the longitudinal axis C toward the proximal-end side with respect to the housing 5, the handle 8 is moved away from the grip 5b.

Therefore, as the end effector 15 is bent toward the bent positions (see FIG. 16B) with respect to the distal end of the sheath 3, the distance between the handle 8 and the stopper 9 in the grip 5b becomes larger than when the end effector 15 is in the neutral position (see FIG. 16A) with respect to the distal end of the sheath 3. Consequently, the handle 8 has a larger movable range in the bent positions than in the neutral position. As the movable range increases, the distance that the slider 37 moves with respect to the first drive shaft 19, i.e., the distance that the resilient member 38 is compressed, increases. Therefore, the axial force F transmitted through the slider 37 to the first drive shaft 19 in the bent positions becomes larger than in the neutral position. The hook pins 95A and 95B and the cavities 11A and 11B thus function as an adjusting mechanism 105 that adjusts the movable range of the slider 37 with respect to the first drive shaft 19 depending on the operated state of the operating member 70. The operating member 100 illustrated in FIGS. 10 through 12 may, of course, be used instead of the operating member 70.

When the operating member 70 is rotated in a direction opposite to the direction described hereinbefore, the first nut 94A is moved along the longitudinal axis C toward the distal-end side and the second nut 94B is moved along the longitudinal axis C toward the proximal-end side. When the second nut 94B is moved along the longitudinal axis C toward the proximal-end side, the second wire 87B is moved along the longitudinal axis C toward the proximal-end side in ganged relation to the second nut 94B. The second hook pin 95B fixed to the second wire 87B presses the wall surface, closest to the proximal-end side, of the second cavity 11B along the longitudinal axis C toward the proximal-end side. The first hook pin 95A fixed to the first wire 87A is moved away from the wall surface, closest to the proximal-end side, of the first cavity 11A toward the distal-end side. Therefore, either when the operating member 70 is turned from the position illustrated in FIG. 16A to the position illustrated in FIG. 16B or when the operating member 70 is turned from the position illustrated in FIG. 16A to a position opposite the position illustrated in FIG. 16B, the actuating mechanism 6 is moved along the longitudinal axis C toward the proximal-end side with respect to the housing 5. Consequently, the handle 8 is moved away from the grip 5b.

Therefore, the adjusting mechanism 105 of the treatment tool 2 according to the present modification is able to adjust the movable range of the slider 37 with respect to the first drive shaft 19 depending on the operated state of the operating member 70. According to the present modification, therefore, there is provided a treatment tool 2 capable of adjusting the axial force that is transmitted to the first drive shaft 19 for opening and closing the pair of grasps 18A and 18B relatively to each other in the case where the end effector 15 is in the neutral position with respect to the sheath 3 and in the case where the end effector 15 is in the bent positions.

Though it has been described hereinbefore that the knob 11 of the rotating mechanism 6C is disposed on the housing 5, the sheath 3 may be integrally connected to the main housing body 5a of the housing 5 and the cavities 11A and 11B may be defined in the main housing body 5a. In such a case, the actuating mechanism 6 cannot be rotated with respect to the housing 5.

Third Embodiment

Next, a third embodiment will hereinafter be described with reference to FIGS. 17A and 17B. The third embodiment represents a modification of the first and second embodiments including various modifications. Those parts which are identical to or those parts which have identical functions to those described in the first and second embodiments are denoted by as identical numeral reference as possible, and will not hereinafter be described in detail.

Figure 17A:
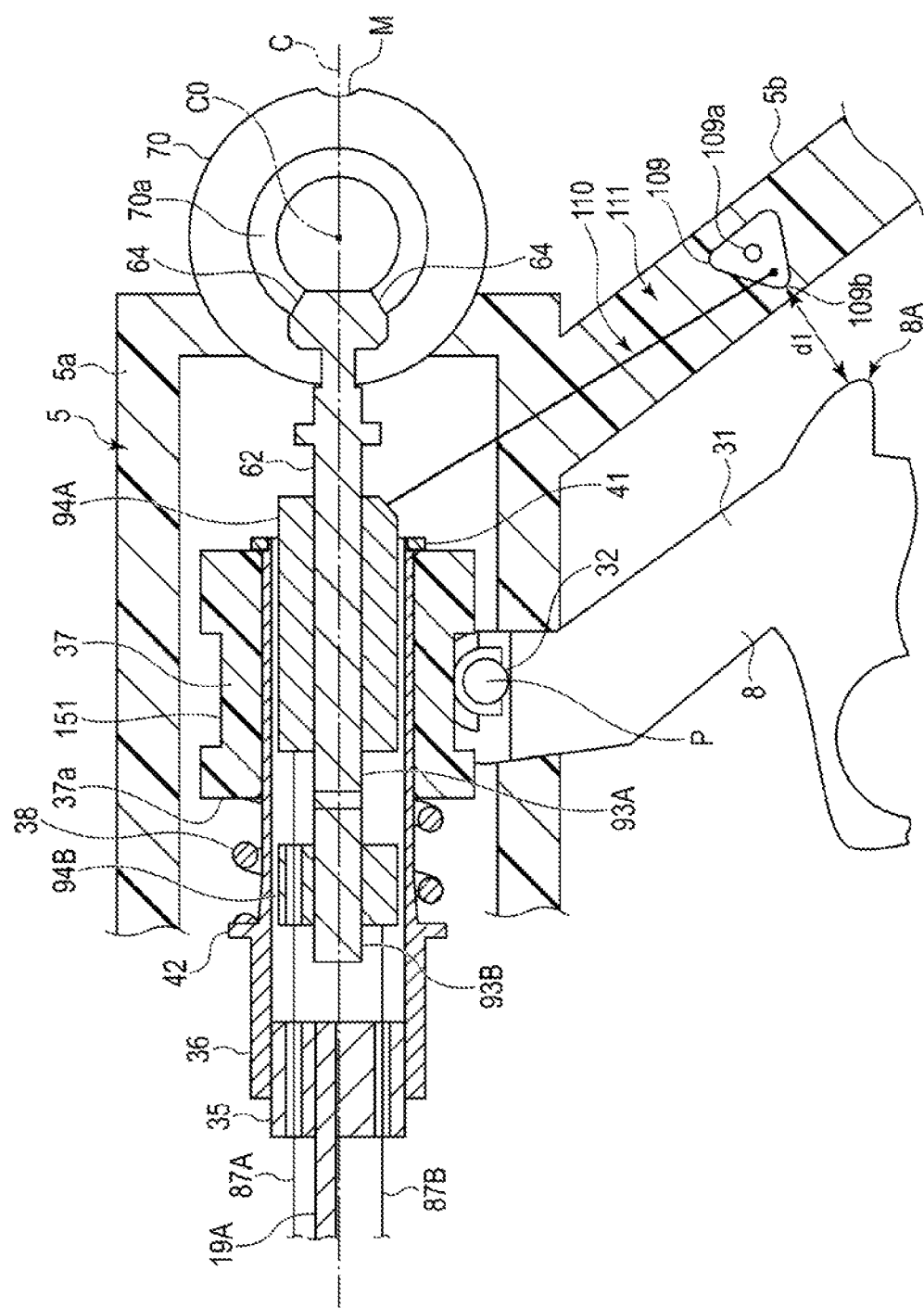
FIG. 17A is a schematic view illustrating a cross section of an actuating mechanism disposed in a housing in a case where an end effector of a treatment tool of a treatment system according to a third embodiment is in a neutral position.
Figure 17B:
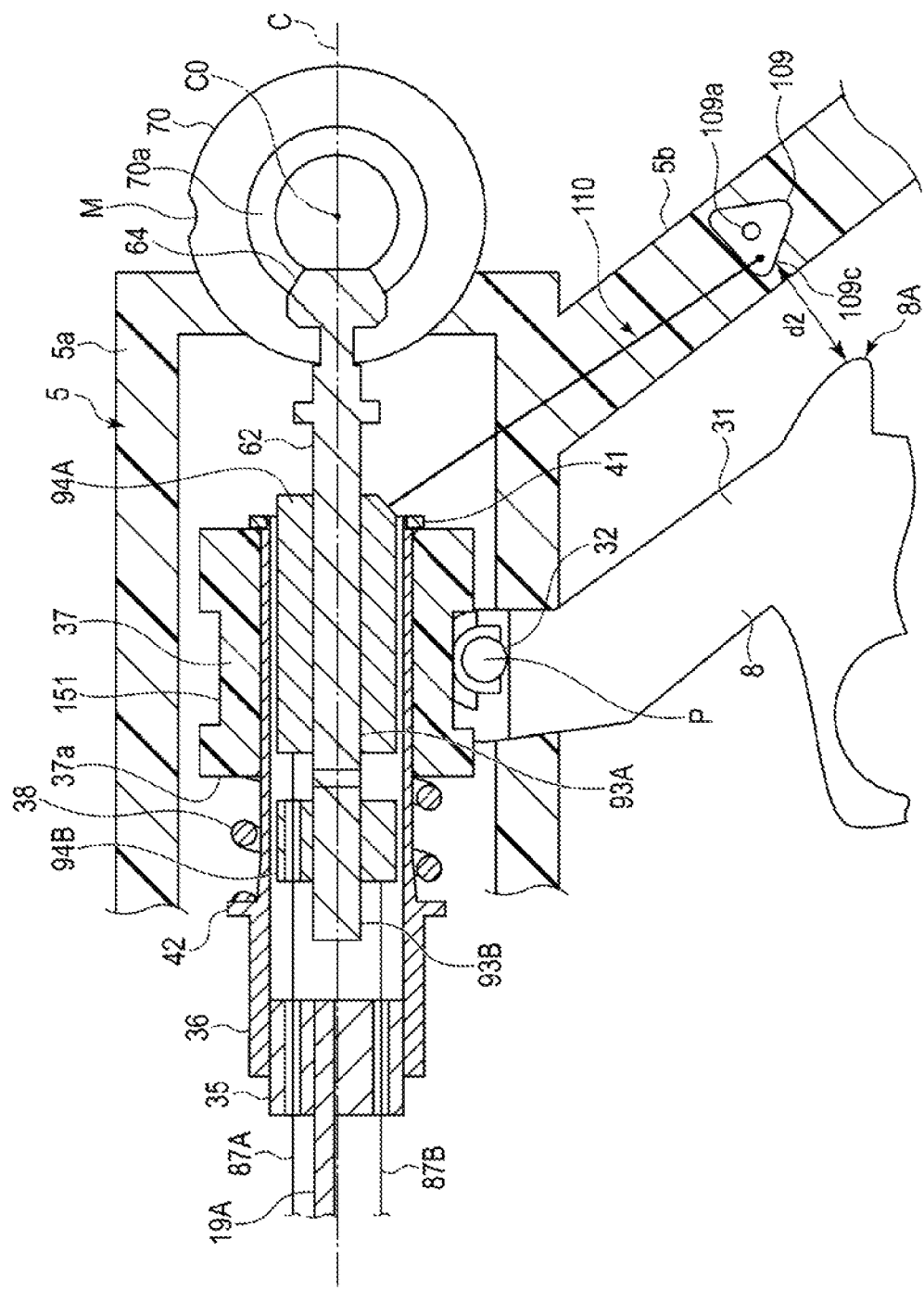
FIG. 17B is a schematic view illustrating a cross section of the actuating mechanism disposed in the housing in a case where the end effector of the treatment tool of the treatment system according to the third embodiment is in a bent position.

As illustrated in FIGS. 17A and 17B, the grip 5b supports a stopper 109 thereon. The stopper 109 is rotatable about the axis of a rotational shaft 109a. The stopper 109 illustrated in FIGS. 17A and 17B is of a substantially triangular shape. However, the stopper 109 may be of any suitable shapes other than a circular shape, including an elliptical shape, a suitable polygonal shape, or the like.

The handle 8 has an abutment portion 8A for abutment against the stopper 109.

The stopper 109 is coupled to the first nut 94A of the bending mechanism 6B of the actuating mechanism 6 through a link 110 in the housing 5. The housing 5 thus has the link 110 between the stopper 109 and the first nut 94A.

In a case where the operating member 70 is in a position illustrated in FIG. 17A, the end effector 15 is in a neutral position. At this time, the distance d1 between the handle 8 and the stopper 109 is the smallest.

In a case where the operating member 70 is in a position illustrated in FIG. 17B, the end effector 15 is in a bent position. At this time, the first nut 94A has been moved along the longitudinal axis C toward the distal-end side, for example. Therefore, the stopper 109 is moved angularly about the axis of the rotational shaft 109a in ganged relation to the movement of the link 110. At this time, a distance d2 between the handle 8 and the stopper 109 is larger than a distance d1 illustrated in FIG. 17A. Consequently, the handle 8 has a larger movable range in the bent positions than in the neutral position. As the movable range increases, the distance that the slider 37 moves with respect to the first drive shaft 19, i.e., the distance that the resilient member 38 is compressed, increases. Therefore, the axial force F transmitted through the slide 37 to the first drive shaft 19 is larger in the bent positions than in the neutral position. The stopper 109 and the link 110 thus function as an adjusting mechanism 111 that adjusts the movable range of the slider 37 with respect to the first drive shaft 19 depending on the operated state of the operating member 70.

When the operating member 70 is rotated in a direction opposite to the direction described hereinbefore, the distance between the handle 8 and the stopper 109 becomes larger than the distance d1. The distance between the handle 8 and the stopper 109 can be equalized to the distance d2 illustrated in FIG. 17B by appropriately shaping the structure of the stopper 109. Therefore, the movable range of the handle 8 increases when the end effector 15 is moved from the neutral position to the bent positions regardless of whether the operating member 70 is turned from the position illustrated in FIG. 17A in one direction or the other.

Therefore, the treatment tool 2 according to the present embodiment is capable of appropriately adjusting the gripping force between the grasps 18A and 18B when the end effector 15 is in the neutral position and when the end effector 15 is in the bent positions, i.e., the first bent position and the second bent position, using the adjusting mechanism 111.

The stopper 109 according to the present embodiment may be used in combination with the mechanism for moving the actuating mechanism 6 with respect to the housing 5, as described according to the first embodiment including various modifications. Though an example in which the stopper 109 is connected to the nut 94A has been described hereinbefore, the stopper 109 may be connected to the second member 46 of the rotor assembly 40 described in the first embodiment, for example. In a case where the end effector 15 is moved from a neutral position to a bent position, the stopper 109 can be rotated about the axis of the rotational shaft 109a as the second member 46 of the rotor assembly 40 rotates about the longitudinal axis C. Therefore, the structure of the stopper 109 according to the present embodiment can be used in the treatment tool 2 described in the first embodiment.

Furthermore, the stopper 109 according to the present embodiment may be used in combination with the mechanism for moving the actuating mechanism 6 with respect to the housing 5 described in the second embodiment including various modifications. Therefore, the structure of the stopper 109 according to the present embodiment can be used in the treatment tool 2 described in the second embodiment.

Modifications

Figure 18:
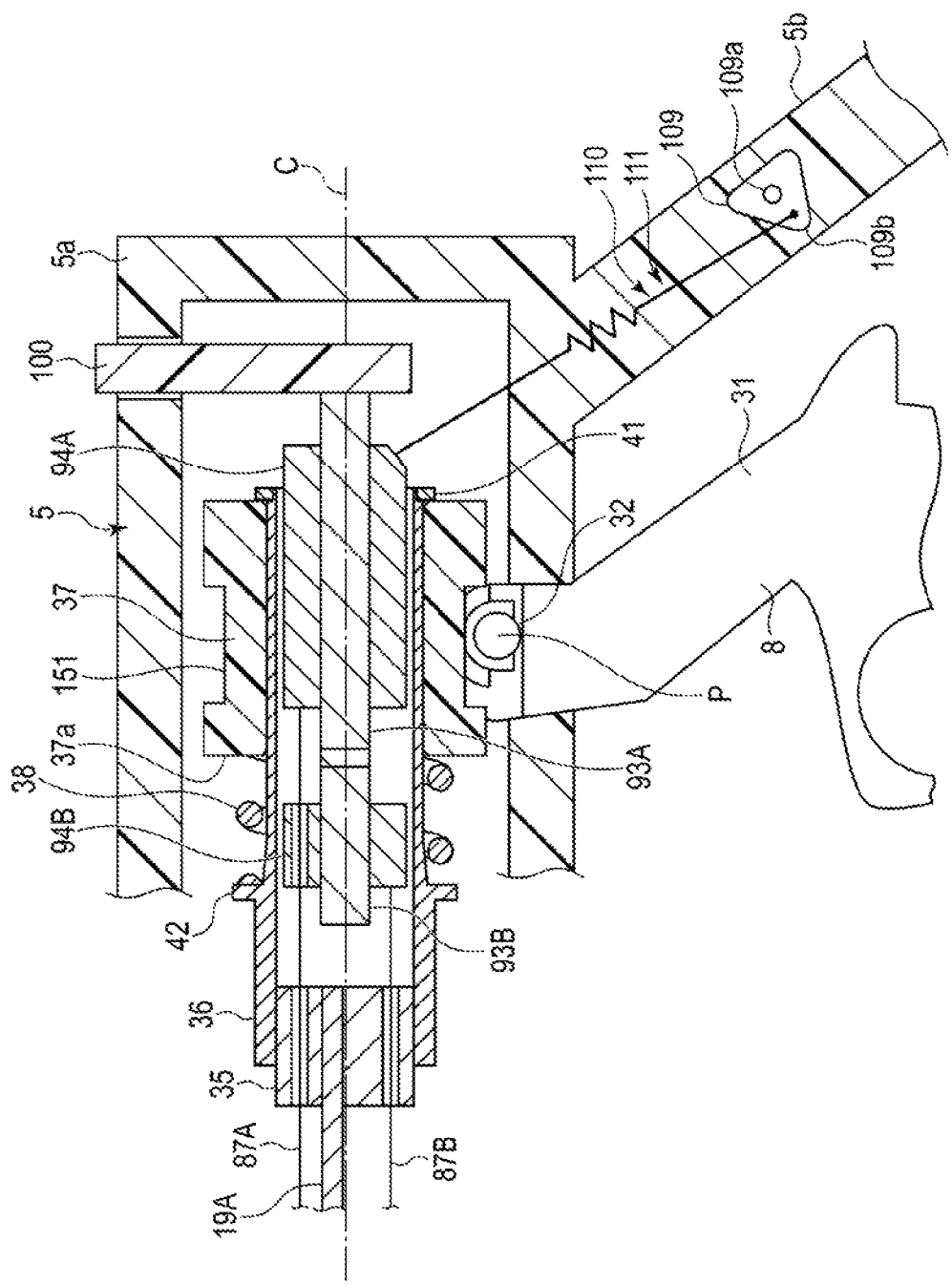
FIG. 18 is a schematic view illustrating a cross section of an actuating mechanism disposed in a housing in a case where an end effector of a treatment tool of a treatment system according to a modification of the third embodiment is in a neutral position.

As illustrated in FIG. 18, an operating member 100 directly connected to the main rotational shaft 62 may be used in place of the operating member 70. In this case, as is the case with the examples illustrated in FIGS. 17A and 17B, the gripping force between the grasps 18A and 18B can be adjusted depending on the bent state of the end effector 15 with respect to the distal end of the sheath 3.

The operating member 100 illustrated in FIGS. 10 through 12 may also be used in place of the operating member 70.

The link 110 should preferably have a damper 110a such as a spring, a pneumatic damper, a hydraulic damper, or the like. In this case, a load is restrained from being applied to the nut 94A, i.e., the actuating mechanism 6, through the link 110 at the time the abutment portion 8A of the handle 8 presses the stopper 109, for example.

The disclosed technology is not limited to the embodiments described hereinbefore and various modifications may be made therein without departing from the scope of the invention when it is reduced to practice. The embodiments may appropriately be combined as much as possible, and the combinations offer combined advantages. Furthermore, the embodiments described hereinbefore include inventions in various stages, and various inventions can be extracted by appropriately combining a plurality of components that are disclosed.

In sum, one aspect of the disclosed technology is directed to a medical instrument comprises a housing and an elongated sheath configured to be attached to the housing. The elongated sheath includes opposed distal end and proximal end along a longitudinal axis. An end effector is configured to be attached to the distal end of the elongated sheath. The end effector includes a pair of grasps. A direction changer used to change a direction of the end effector with respect to the distal end of the elongated sheath. A first drive shaft movable in the elongated sheath in ganged relation for opening and closing movement of the pair of grasps. A second drive shaft movable in the elongated sheath in ganged relation for angular movement of the end effector by the direction changer with respect to the elongated sheath. An operating member is configured to actuate the second drive shaft between bent positions to which the end effector is angularly moved and a neutral position to which the end effector extends along the longitudinal axis with respect to the sheath. A slider is movable with respect to the first drive shaft. An adjusting mechanism adjusts a movable range of the slider with respect to the first drive shaft depending on an operated state of the operating member.

The adjusting mechanism operates in response to an operation input applied to the operating member. The adjusting mechanism includes a gear assembly transmitting the operation input applied to the operating member to the second drive shaft. The medical instrument further comprises a handle in which the slider has a groove defined therein around the longitudinal axis. The handle is fitted in the groove. The adjusting mechanism includes a gear assembly transmitting the operation input applied to the operating member to the slider so as to rotate the slider about the longitudinal axis, thereby changing a relative positional relationship between the groove and the handle. The groove has a width along the longitudinal axis and the width varies around the longitudinal axis of the sheath. A position at which the handle is fitted in the groove varies depending on rotation with respect to the slider. The gear assembly is fitted in the slider and rotates the slider about the longitudinal axis in response to the operation input applied to the operating member. The medical instrument further comprises a handle being attached to the housing. The adjusting mechanism has an engaging portion adjusting a positional relationship between the housing and the handle.

The engaging portion has a first engaging portion disposed on the housing and a second engaging portion disposed on the operating member and engaged by the first engaging portion. The housing is moved along the longitudinal axis with respect to the operating member depending on a position in which the first engaging portion and the second engaging portion engage with one another. The medical instrument of further comprises a stopper that defines a movable range of the handle. The handle is supported on the housing. The engaging portion moves along the longitudinal axis with respect to the housing in ganged relation to the second drive shaft, thereby adjusting the positional relationship between the housing and the handle. The medical instrument further comprises a handle in which the adjusting mechanism includes a stopper movable in ganged relation to movement of the second drive shaft along the longitudinal axis to limit a movable range of the handle. The adjusting mechanism is arranged such that a movable range of the slider along the longitudinal axis is larger in the bent position than in the neutral position. The operating member is rotatable about a predetermined rotational axis. The adjusting mechanism adjusts an axial force applied to the first drive shaft between the neutral position and the bent position. The adjusting mechanism adjusts the axial force applied to the first drive shaft between the neutral position and the bent positions such that the axial force is larger.

Another aspect of the disclosed technology is directed to a medical instrument comprises a housing having a grip integrally attached thereto. A movable handle is attached to the housing and is angularly movable with respect to the housing. An elongated sheath having respective distal and proximal ends along a longitudinal axis. The elongated sheath is attached to the housing via the proximal end. An end effector is configured to be attached to the distal end of the elongated sheath. The end effector includes a pair of grasps. A direction changer changes a direction of the end effector with respect to the distal end of the elongated sheath. A first drive shaft is movable in the elongated sheath in ganged relation for opening and closing movement of the pair of grasps. A second drive shaft is movable in the elongated sheath in ganged relation for angular movement of the end effector by the direction changer with respect to the elongated sheath. An operating member is configured to actuate the second drive shaft between bent positions to which the end effector is angularly moved and a neutral position in which the end effector extends along the longitudinal axis with respect to the sheath. A slider being movable with respect to the first drive shaft. An adjusting mechanism adjusts a movable range of the slider with respect to the first drive shaft depending on an operated state of the operating member. The medical instrument further comprises a power supply device being attached to the housing via a cable. The medical instrument further includes an operating device such as a foot switch configured to be attached to the power supply device.

A further aspect of the disclosed technology is directed to a treatment tool comprises a medical instrument. The medical instrument includes a power supply device and a housing is attached to the power supply device. The housing having a grip integrally attached thereto. A movable handle is attached to the housing and is angularly movable with respect to the housing. An elongated sheath having respective distal and proximal ends along a longitudinal axis. The elongated sheath is attached to the housing via the proximal end. An end effector is configured to be attached to the distal end of the elongated sheath. The end effector includes a pair of grasps. A direction changer changes a direction of the end effector with respect to the distal end of the elongated sheath. A first drive shaft being movable in the elongated sheath in ganged relation for opening and closing movement of the pair of grasps. A second drive shaft being movable in the elongated sheath in ganged relation for angular movement of the end effector by the direction changer with respect to the elongated sheath. An operating member is configured to actuate the second drive shaft between bent positions to which the end effector is angularly moved and a neutral position in which the end effector extends along the longitudinal axis with respect to the sheath. A slider being movable with respect to the first drive shaft and an adjusting mechanism adjusts a movable range of the slider with respect to the first drive shaft depending on an operated state of the operating member. The slider has a groove defined therein around the longitudinal axis. The movable handle is fitted in the groove and the adjusting mechanism includes a gear assembly transmitting an operation input applied to the operating member to the slider so as to rotate the slider about the longitudinal axis, thereby changing a relative positional relationship between the groove and the handle.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent.

Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. A medical instrument comprising:
    a housing;
    an elongated sheath configured to be attached to the housing, the elongated sheath including opposed distal end and proximal end along a longitudinal axis;
    an end effector configured to be attached to the distal end of the elongated sheath, the end effector including a pair of grasps;
    a direction changer configured to change a direction of the end effector with respect to the distal end of the elongated sheath;
    a first drive shaft movable in the elongated sheath in ganged relation for opening and closing movement of the pair of grasps;
    a second drive shaft movable in the elongated sheath in ganged relation for angular movement of the end effector by the direction changer with respect to the elongated sheath;
    an operating member configured to actuate the second drive shaft between bent positions to which the end effector is angularly moved and a neutral position to which the end effector extends along the longitudinal axis with respect to the sheath;
    a slider being movable with respect to the first drive shaft; and
    an adjusting mechanism configured to adjust a movable range of the slider with respect to the first drive shaft depending on an operated state of the operating member.

2. The medical instrument of claim 1, wherein
the adjusting mechanism is configured to operate in response to an operation input applied to the operating member.

3. The medical instrument of claim 2, wherein
the adjusting mechanism includes a gear assembly configured to transmit the operation input applied to the operating member to the second drive shaft.

4. The medical instrument of claim 2 further comprising:
a handle,
wherein
the slider has a groove defined therein around the longitudinal axis, the handle being fitted in the groove, and
the adjusting mechanism includes a gear assembly configured to transmit the operation input applied to the operating member to the slider so as to rotate the slider about the longitudinal axis, thereby changing a relative positional relationship between the groove and the handle.

5. The medical instrument of claim 4, wherein
the groove has a width along the longitudinal axis, and the width varies around the longitudinal axis of the sheath, and
a position at which the handle is fitted in the groove varies depending on rotation with respect to the slider.

6. The medical instrument of claim 5, wherein
the gear assembly is fitted in the slider and is configured to rotate the slider about the longitudinal axis in response to the operation input applied to the operating member.

7. The medical instrument of claim h further comprising:
a handle being attached to the housing,
wherein the adjusting mechanism has an engaging portion configured to adjust a positional relationship between the housing and the handle.

8. The medical instrument of claim 7, wherein
the engaging portion has a first engaging portion disposed on the housing and a second engaging portion disposed on the operating member and engaged by the first engaging portion; and
the housing is moved along the longitudinal axis with respect to the operating member depending on a position in which the first engaging portion and the second engaging portion engage with one another.

9. The medical instrument of claim 7 further comprising:
a stopper that defines a movable range of the handle;
wherein
the handle is supported on the housing, and
the engaging portion moves along the longitudinal axis with respect to the housing in ganged relation to the second drive shaft, thereby adjusting the positional relationship between the housing and the handle.

10. The medical instrument of claim 1 further comprising:
a handle;
wherein the adjusting mechanism includes a stopper movable in ganged relation to movement of the second drive shaft along the longitudinal axis to limit a movable range of the handle.

11. The medical instrument of claim 1, wherein
the adjusting mechanism is arranged such that a movable range of the slider along the longitudinal axis is larger in the bent position than in the neutral position.

12. The medical instrument of claim 1, wherein the operating member is rotatable about a predetermined rotational axis.

13. The medical instrument of claim 1, wherein
the adjusting mechanism is configured to adjust an axial force applied to the first drive shaft between the neutral position and the bent position.

14. The medical instrument of claim 13, wherein
the adjusting mechanism is configured to adjust the axial force applied to the first drive shaft between the neutral position and the bent positions such that the axial force is larger.

15. A medical instrument comprising:
a housing having a grip integrally attached thereto, a movable handle being attached to the housing and being angularly movable with respect to the housing;
an elongated sheath having respective distal and proximal ends along a longitudinal axis, the elongated sheath being attached to the housing via the proximal end;
an end effector configured to be attached to the distal end of the elongated sheath, the end effector including a pair of grasps;
a direction changer configured to change a direction of the end effector with respect to the distal end of the elongated sheath;
a first drive shaft being movable in the elongated sheath in ganged relation for opening and closing movement of the pair of grasps;
a second drive shaft being movable in the elongated sheath in ganged relation for angular movement of the end effector by the direction changer with respect to the elongated sheath;
an operating member configured to actuate the second drive shaft between bent positions to which the end effector is angularly moved and a neutral position in which the end effector extends along the longitudinal axis with respect to the sheath;
a slider movable with respect to the first drive shaft; and
an adjusting mechanism configured to adjust a movable range of the slider with respect to the first drive shaft depending on an operated state of the operating member.

16. The medical instrument of claim 15 further comprising a power supply device being attached to the housing via a cable.

17. The medical instrument of claim 16, further comprising an operating device configured to be attached to the power supply device.

18. A treatment tool comprising:
the medical instrument of claim 15,
wherein:
the medical instrument further comprises a power supply device;
the housing is attached to the power supply device.

19. The treatment tool of claim 18, wherein
the slider has a groove defined therein around the longitudinal axis, the movable handle being fitted in the groove, and
the adjusting mechanism includes a gear assembly configured to transmit an operation input applied to the operating member to the slider so as to rotate the slider about the longitudinal axis, thereby changing a relative positional relationship between the groove and the handle.

20. A medical instrument comprising:
a housing;
an elongated sheath configured to be attached to the housing, the elongated sheath including opposed distal and proximal ends along a longitudinal axis;

an end effector attached to the distal end of the elongated sheath so as to allow angular movement of the end effector with respect to the elongated sheath, the end effector including a pair of grasps;

a first drive shaft movable in the elongated sheath in ganged relation for opening and closing movement of the pair of grasps;

a second drive shaft movable in the elongated sheath in ganged relation for angular movement of the end effector with respect to the elongated sheath;

a dial configured to actuate the second drive shaft between bent positions to which the end effector is angularly moved and a neutral position to which the end effector extends along the longitudinal axis with respect to the sheath; and a slider being movable with respect to the first drive shaft, wherein a movable range of the slider with respect to the first drive shaft depends on an operated state of the dial.

* * * * *